United States Patent [19]

Kikuchi et al.

[11] Patent Number: 5,443,959
[45] Date of Patent: Aug. 22, 1995

[54] METHOD OF ASSAYING FIBRINOGEN, DRY REAGENT THEREFOR, AND PROCESS FOR THE PREPARATION THEREOF

[75] Inventors: Masayoshi Kikuchi, Tsukuba; Kenji Kunai, Ushiku; Takafumi Yamada, Sagamihara, all of Japan

[73] Assignee: Tokuyama Corporation, Yamaguchi, Japan

[21] Appl. No.: 98,825

[22] Filed: Jul. 29, 1993

[30] Foreign Application Priority Data

Sep. 9, 1992 [JP] Japan .................. 4-240681
Nov. 12, 1992 [JP] Japan .................. 4-302368
Jan. 19, 1993 [JP] Japan .................. 5-006646

[51] Int. Cl.$^6$ ............. C12Q 1/56; G01N 33/86; C07K 14/75
[52] U.S. Cl. ................. 435/13; 435/214; 436/46; 436/69; 530/381; 530/382; 530/383; 530/384; 422/73
[58] Field of Search ........ 435/13, 214; 436/46, 436/69; 530/381, 382, 383, 384; 422/73

[56] References Cited

U.S. PATENT DOCUMENTS

| | | | |
|---|---|---|---|
| 4,849,340 | 7/1989 | Oberhardt | 435/13 |
| 5,059,525 | 10/1991 | Bartl et al. | 435/13 |
| 5,110,727 | 5/1992 | Oberhardt | 435/13 |

FOREIGN PATENT DOCUMENTS

WO92/01065 1/1992 WIPO .

OTHER PUBLICATIONS

Oberhardt et al, *Clin. Chem*, vol. 37, No. 4, pp. 520–526, 1991.
Gorczynsha et al, *Chemical Abstracts*, vol. 101, p. 419, Ref. No. 213072, 1984.
Sane et al, *Biological Abstracts*, vol. 94, No. 1, Ref. No. 8551, 1992.

*Primary Examiner*—Michael G. Wityshyn
*Assistant Examiner*—Abdel A. Mohamed
*Attorney, Agent, or Firm*—Wenderoth, Lind & Ponack

[57] ABSTRACT

A dry reagent consisting essentially of (a) a protein having thrombin activity, (b) at least one additive selected from the group consisting of amino acid, a salt thereof and saccharide and optionally (c) magnetic particles, and a method of assaying fibrinogen in an assay sample using the above dry reagent. The dry reagent obviates the time required for preparing a reagent and warming an assay sample, and permits facile fibrinogen assay by only diluting an assay sample. The fibrinogen assay range being broad, the dry reagent substantially obviates the procedure of remeasuring plasma having a fibrinogen concentration outside the assay range of a liquid reagent. The assay result by the dry reagent and that by a liquid reagent well correlate with each other as compared with the result by any known thrombin-containing dry reagent, and the assay by the dry reagent can be performed with good reproducibility in achievement and reliability in measurement.

22 Claims, 20 Drawing Sheets

INLET FOR FINAL SOLUTION OF DRY REAGENT
D
INLET FOR PLASMA

FIG. 4-A
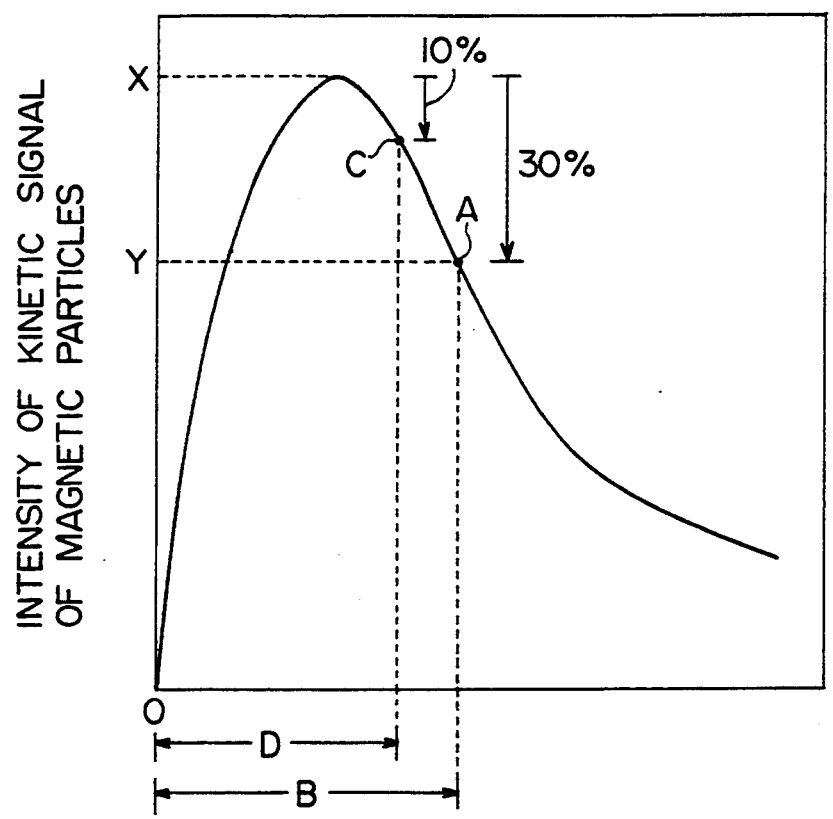
FIG. 4-B
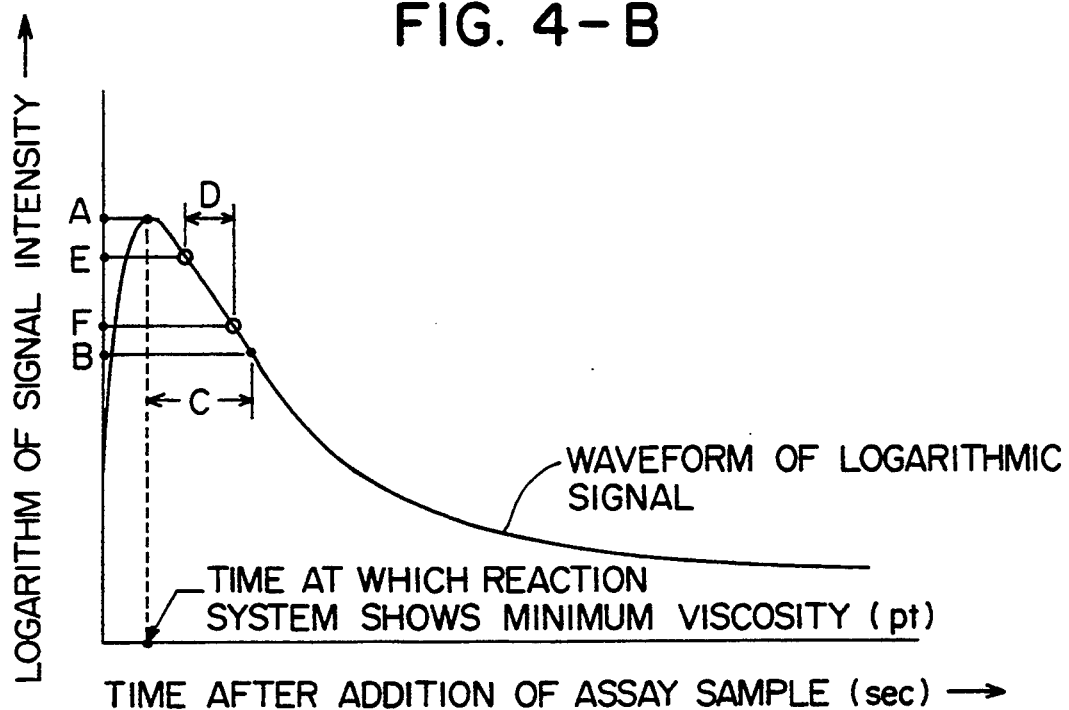

NUMBER OF ASSAY SAMPLES = 41

REGRESSION LINE

Y = 0.9925X + 8.6531

CORRELATION COEFFICIENT = 0.9763

CONCENTRATION OF FIBRINOGEN IN PLASMA (mg/dl)

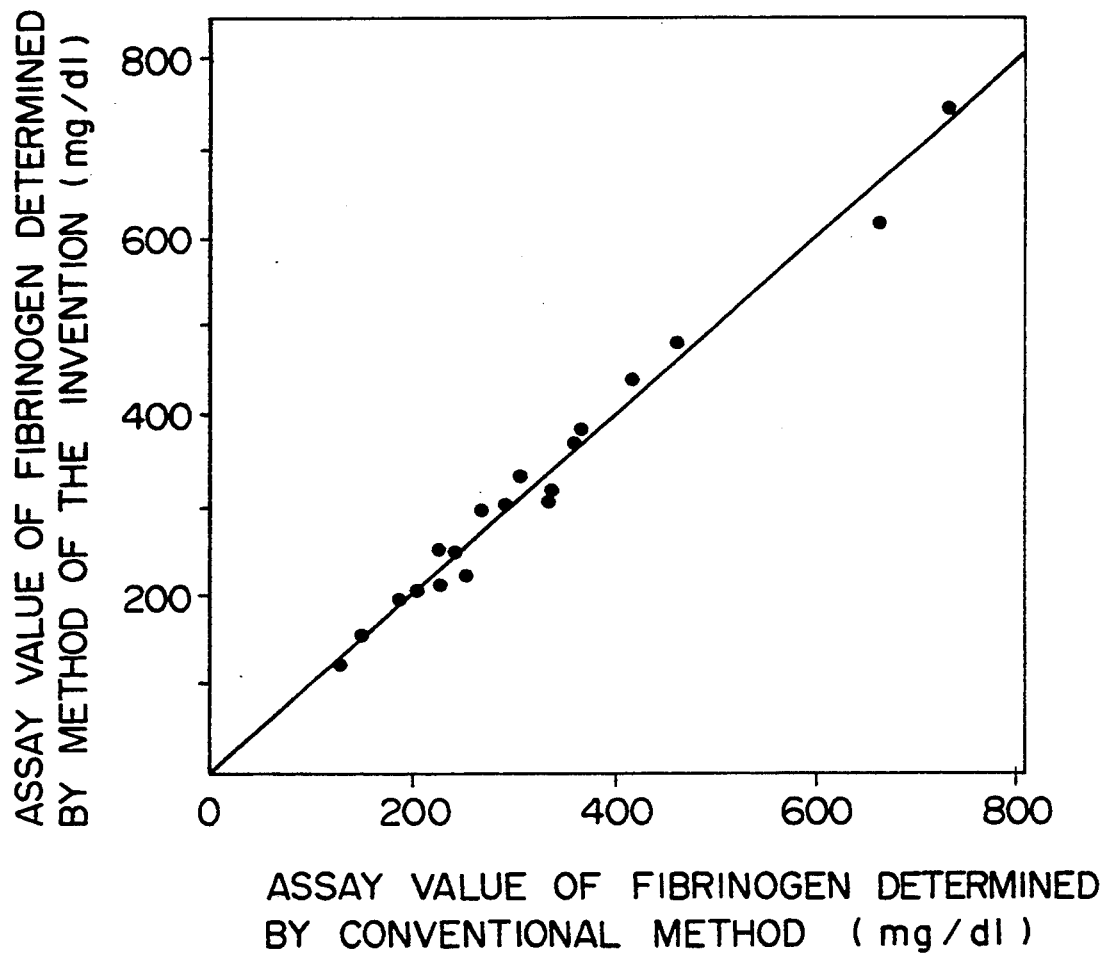

METHOD OF ASSAYING FIBRINOGEN, DRY REAGENT THEREFOR, AND PROCESS FOR THE PREPARATION THEREOF

The present invention relates to a method of assaying fibrinogen in an assay sample, a dry reagent therefor and a process for the preparation of the dry reagent. More specifically, it relates to a method of assaying fibrinogen in an assay sample by simple means promptly with good reproducibility, and a series of techniques related thereto.

PRIOR ART

Fibrinogen assay and determinations of an activated partial thromboplastin time (hereinafter abbreviated as "APTT") and a prothrombin time (hereinafter abbreviated as "PT") as well are carried out for testing blood for abnormal or normal coagulation or urgency of a patient suffering an excessive loss of blood.

A conventional fibrinogen assay method is broadly classified into a method using a thrombin-containing reagent in a liquid form (hereinafter referred to as "liquid reagent") and a method using a dry reagent containing thrombin.

The method using a liquid reagent includes a thrombin time method, a weight method, a salting out method, a method using an antifibrinogen antibody and an aggregation method using latex particles.

In the salting out method and the method using an antifibrinogen antibody, the amount of fibrinogen as an antigen in an assay sample is measured, and molecules other than intact fibrinogen such as products formed by degradation of fibrinogen are also measured together. Hence, these methods are not used for a general blood coagulation test to determine a normal or abnormal blood coagulation capability.

In the weight method, thrombin is added to plasma to react the thrombin with fibrinogen, and the weight of formed fibrin mass is directly measured. This method is rarely used since the handling is complicated and the measured value is sometimes irregular.

The assay method according to the aggregation method using latex particles is disclosed, for example, in Japanese Laid-open Patent Publication No. 4551/1982. Said assay method uses the high affinity of a fibrin monomer to latex particles. That is, serial diluted plasma solutions are first prepared, a suspension of latex particles is added to, and mixed with, each diluted plasma solution, and the mixtures are cultured. Then, the aggregation of the latex particles is monitored and the titer is recorded. On the other hand, a thrombin-containing suspension of latex particles is added to the same diluted plasma solutions, and the mixtures are cultured. The aggregation of tile latex particles is monitored, and the titer is recorded. The former titer corresponds to the concentration of a fibrin monomer in the plasma, and the latter titer corresponds to the sum total of the concentration of fibrinogen in the plasma and the concentration of a fibrin monomer in the plasma. Therefore, the concentration of fibrinogen is calculated by deducting the former titer from the latter titer. This assay method is useful for simultaneously assaying a fibrin monomer and fibrinogen in a plasma, while it disadvantageously cannot be used as an urgent test since it requires a considerably long period of time from the initiation of measurement to the calculation of a fibrinogen concentration and since the reagent preparation takes time.

In the fibrinogen assay method using a liquid reagent, a thrombin time method discovered by Clauss (Clauss A, Gerinungsphislologishe Schneiomethode zur Bestimung des Fibrinogens, Acta Heamat, vol. 17, p. 237, 1957) is generally used. This fibrinogen assay method uses the dependency of the rate of the conversion of fibrinogen to fibrin in the presence of a surplus amount of thrombin mainly upon a fibrinogen concentration.

In the above assay method, the measurement is carried out by diluting an assay sample with any buffer solution, preheating the resultant diluted liquid, adding a liquid reagent containing thrombin and measuring a coagulation time. In this measurement, optical measurement to detect an attenuation of transmitted light or physical measurement to detect an increase in viscosity is performed up to a predetermined end point. The coagulation time in this method refers to a time required from the addition of a thrombin liquid reagent to the above end point. In this assay method, a fibrinogen concentration is determined on the basis of the above coagulation time.

The thrombin reagent used In the thrombin time method and the above assay method is generally widely used for assaying fibrinogen. However, fibrinogen assay methods using the thrombin reagent have the following defects. The thrombin reagent is first prepared by restoring the same from a freeze-dried one with distilled water (the restored liquid reagent is poor in shelf life when stored for a long period of time). It is required to preheat a diluted assay sample liquid. Time is thus required prior to the measurement. Further, the range of the concentration at which an assay sample can be assayed is narrow. Therefore, when the assay sample has a fibrinogen concentration lower than the above assay concentration range, it is necessary to decrease the dilution degree for further measurement. When the assay sample has a fibrinogen concentration higher than the above assay concentration range, it is then necessary to increase the dilution degree for further measurement.

On the other hand, the method using a dry reagent containing thrombin has been recently proposed, and it is disclosed in U.S. Pat. No. 5,110,727 (PCT Laid-open Publication No. WO 89/10788).

The above Publication describes a dry reagent containing magnetic particles, used in coagulation assay for measurement of various coagulation and clot lysis factors, and use thereof.

The thrombin-containing dry reagent described in the above Publication is prepared by mixing a thrombin reagent solution and a plasminogen reagent solution, further adding magnetic particles, pouring a predetermined amount of the resultant solution mixture onto a reaction slide and then freeze-drying the solution mixture. When the above dry reagent is used for measuring a fibrinogen concentration, the measurement is carried out by placing the thrombin-containing dry reagent on a reaction holding means, adding a predetermined amount of plasma to the thrombin-containing dry reagent, applying a combination of a vibrating magnetic field with a static permanent magnetic field immediately after the above addition, thereby to put the magnetic particles in motion and optically monitoring the motion signal of the magnetic particles. The above Publication suggests that the plasma can be measured for a fibrinogen concentration and a plasminogen activator concentration at the same time by utilizing the correspondence of the decrease and increase of this motion signal to the viscosity increase and decrease in the dry reagent. That is, according to the above Publication, it is suggested that the negative slope of the motion signal which the magnetic particles show immediately after the addition of plasma is in proportion to the fibrinogen concentration in the plasma and that the lysis initiation time at which the motion signal of the magnetic particles restarts to increase after having arrived at a plateau is in inverse proportion to the plasminogen activator concentration in the plasma. However, the above Publication does not specifically explain anything concerning the technical means for the fibrinogen assay method using the dry reagent and its effects, nor does it describe anything concerning the correlation to the assay method using a liquid reagent.

As described above, if fibrinogen can be assayed with a dry reagent containing thrombin, the present problem that time needs to lapse before the measurement can be overcome. The present inventors have prepared a dry reagent according to U.S. Pat. No. 5,110,727 and measured a plasma for a fibrinogen concentration using the dry reagent. As a result, however, it has been found that the obtained size of negative slope of the motion signal of the magnetic particles does not show sufficient reproducibility. It has been further found that when plasmas having known fibrinogen concentrations are measured several times according to the above method, the obtained size of negative slope of the motion signal of the magnetic particles does not correspond to the fibrinogen concentration in some cases.

It has been therefore found to be difficult to put the fibrinogen assay method to practical use according to the method disclosed in U.S. Pat. No. 5,110,727.

SUMMARY OF THE INVENTION

It is a first object of the present invention to provide a dry reagent with which fibrinogen in an assay sample can be accurately assayed in a short period of time, and an assay method.

It is a second object of the present invention to provide a dry reagent which permits the facile assay of fibrinogen in an assay sample with good reproducibility, and an assay method.

It is a third object of the present invention to provide a dry reagent for assaying fibrinogen in an assay sample, which maintains sensitivity, reproducibility and accuracy even when stored for a long period of time, and a reaction slide containing said dry reagent.

It is further another object of the present invention to provide a facile means by which fibrinogen in an assay sample can be accurately assayed, and a reagent used therefor.

It is still further another object of the present invention to provide a reagent for fibrinogen assay, which can be advantageously used for an urgent test of blood in a blood sample for normal or abnormal coagulation in an excessive loss of blood, and an assay method.

Other objects and advantages of the present invention will be apparent from the following description.

The present inventors have made diligent studies to achieve the above objects of the present invention, and have found that the solubility of a dry reagent containing a protein having thrombin activity in an assay sample liquid greatly affects the very assay performance of fibrinogen. That is, it has been revealed that the uniformity of dry reagent dissolution in the assay sample liquid affects the reproducibility in fibrinogen assay and further that improvement in the solubility of the dry reagent finally broadens the fibrinogen assay range. And, it has been further revealed that the uniformity and improvement of the solubility of the dry reagent can be achieved by using a specific additive and that the inhibition of the coagulation reaction of fibrinogen is not caused in the presence of this specific additive.

According to the present invention, some of the above objects of the present invention are achieved by a dry reagent (I) for fibrinogen assay, consisting essentially of:

(a) a protein having thrombin activity (component a),
(b) at least one additive selected from the group consisting of amino acid, a salt thereof and saccharide (component b), and
(c) magnetic particles (component c).

According to the present invention, some of the above objects of the present invention are achieved by a dry reagent (II) for fibrinogen assay, consisting essentially of:

(a) a protein having thrombin activity (component a) and
(b) at least one additive selected from the group consisting of amino acid, a salt thereof and saccharide (component b).

According to the present invention, some of the above objects of the present invention are achieved by a method of assaying fibrinogen in an assay sample, comprising:

(1) bringing the above dry reagent (I) and an assay sample into contact with each other,
(2) monitoring the viscosity of the dry reagent up to an end point which is arbitrarily set at a point where the viscosity of the dry reagent increases to be 20/19 to 3 times as large as the minimum value of the viscosity thereof,
(3) measuring a coagulation time which has lapsed from the contact of the dry reagent and the assay sample to the end point, and
(4) determining an active fibrinogen content in the assay sample on the basis of the coagulation time.

The fibrinogen assay method according to the present invention is based on the thrombin time method, and the fibrinogen measured by the fibrinogen assay method of tile present invention is fibrinogen capable of converting itself into fibrin in the presence of thrombin.

DETAILED DESCRIPTION OF THE INVENTION

The dry reagents (I) and (II), the processes for the production thereof and the method of assaying fibrinogen in an assay sample, according to the present invention, will be explained in detail and specifically.

Dry Reagents (I) and (II) for Fibrinogen Assay

The dry reagents (I) and (II) of the present invention contain, as component a, a protein having thrombin activity, and this protein refers to a protein which catalyzes the conversion of fibrinogen to fibrin. The origin of this protein is not specially limited as far as it can catalyze the above conversion to fibrin. This protein is generally advantageously selected from bovine thrombin, human thrombin and snake venom protein. The protein having thrombin activity is generally commercially available as freeze-dried products, and these can be conveniently used as such.

The amount of the protein as component a in the dry reagent (I) for fibrinogen assay per 25 $\mu$l of a diluted assay sample used in one measurement (per one reaction slide to be described later) is generally properly at least 0.05 NIHU, preferably 0.5 to 1.5 NIHU. The "NIHU" is a unit (National Institutes of Health Unit) for an amount of thrombin activity and is generally known. It is described, for example, in "Minimum Requirement for Dried Thrombin" 2nd Revision, Division of Biologic Standards, National Institutes of Health, Bethesda, Md., 1946.

In explanations of the dry reagent (I) for fibrinogen assay and the process for the production thereof, provided by the present invention, the proportions of the components a, b and c refer to their amounts used per 25 $\mu$l of a diluted assay sample used in one measurement (e.g., per one reaction slide). Therefore, the proportions of these components can be determined depending upon the ordinary amount of an assay sample, and can be varied relative to the amount of a diluted assay sample.

On the other hand, concerning the dry reagent (II) for fibrinogen assay, provided by the present invention, a diluted assay sample is generally used in an amount of about 300 $\mu$l for one measurement, and the amount of the protein (component a) per 300 $\mu$l of a diluted assay sample is generally properly at least 0.5 NIHU, preferably 5 to 15 NIHU. In explanations of the dry reagent (II) for fibrinogen assay and the process for the production thereof, provided by the present invention, the proportions of the components a, b and c refer to their amounts used per 300 $\mu$l of a diluted assay sample used in one measurement. Therefore, the proportions of these components can be varied relative to the amount of an assay sample.

The dry reagents (I) and (II) of the present invention contain, as component b, at least one additive selected from the group consisting of amino acid, a salt thereof and saccharide. As the amino acid or salt thereof, preferred is $\alpha$-amino acid or a salt thereof. The above amino acid or salt thereof can be selected from neutral amino acid or a salt thereof, acidic amino acid or a salt thereof, and a basic amino acid or a salt thereof. Of these, acidic amino acid or a salt thereof is preferred for the following reasons. When acidic amino acid or a salt thereof is used, the solubility of an assay sample in tile dry reagents (I) and (II) is excellent, and tile motion signal of the magnetic particles is excellent in reproducibility. Typical examples of the acidic amino acid or the salt thereof include glutamic acid, sodium glutamate, aspattic acid and sodium aspartate. Examples of the neutral amino acid or the salt thereof include glycin, glycin hydrochloride and L-alanine. Examples of the basic amino acid or the salt thereof include L-lysine, L-lysine hydrochloride and L-arginine.

When amino acid is used as component b, generally, the acidic amino acid is neutralized to pH 6.0 to 8.0 with a proper base such as sodium hydroxide or potassium hydroxide before use, and the basic amino acid is neutralized to pH 6.0 to 8.0 with a proper acid such as hydrochloric acid or acetic acid before use.

The saccharide is selected from monosaccharide and polysaccharide, while monosaccharide is preferred since the motion signal of the magnetic particles is excellent in reproducibility. Typical examples of the monosaccharide include glucose and fructose. Examples of the polysaccharide include sucrose, lactose, trehalose and dextrin. Of these saccharides, glucose, fructose and sucrose are preferred.

In the dry reagent (I) and the process for the production thereof, provided by the present invention, the amount of the component b is preferably 0.02 to 1 mg, more preferably 0.2 to 0.8 mg.

In the dry reagent (II) and the process for the production thereof, provided by the present invention, the amount of the component b is preferably 0.2 to 10 mg, more preferably 2.0 to 8.0 mg.

The dry reagent for fibrinogen assay, provided by the present invention, contains magnetic particles as component c. This component c is useful for optically monitoring a change in the viscosity of the reagent as a motion signal in the process of conversion of fibrinogen to fibrin. Known magnetic particles can be used as the component c without any limitation. For example, the component c is selected from ferrosoferric oxide particles, ferric oxide particles, iron particles, cobalt particles, nickel particles and chromium oxide particles. Preferred are ferrosoferric oxide particles in view of the intensity of motion signal of the magnetic particles. The average particle diameter of the magnetic particles is not specially limited, and it is generally 0.01 to 10 $\mu$m, preferably 0.1 to 3 $\mu$m. The content of the magnetic particles in the dry reagent (I) is not specially limited, and it is generally $2\times10^{-6}$ g to $2\times10^{-4}$ g, preferably $2\times10^{-5}$ g to $1.2\times10^{-4}$ g.

When the component b, i.e., the above amino acid, salt thereof or saccharide, is not contained, the reagent is poor in solubility. As a result, the motion signal of tile magnetic particles is not obtained and hence, the assay cannot be effectively carried out. Further, when an additive other than these is used, the reagent is poor in solubility, and in some case, no motion signal of the magnetic particles is obtained. Even when a motion signal is obtained, the solubility of the reagent varies, and as a result, no reproducibility in the change of the motion signal with time is observed. As a consequence, no accurate assay can be performed with good reproducibility. Further, due to the component b, the inhibition of the coagulation reaction of fibrinogen is not caused, and as a result, the facile and accurate assay of fibrinogen can be carried out. As the component b, generally, the amino acid or salt thereof rather than saccharide is excellent in view of the solubility of the reagent, reproducibility and facilitation of the reaction.

Preparations of Dry Reagent for Fibrinogen Assay and Materials for the Dry Reagent According to the present invention, there is provided a process for tile production of the above dry reagent (I) for fibrinogen assay, comprising freeze-drying a mixed liquid consisting essentially of:
 (a) a protein having thrombin activity (component a),
 (b) at least one additive selected from the group consisting of amino acid, a salt thereof and saccharide (component b),
 (c) magnetic particles (component c), and
 (d) water-based medium (component d).

Further, according to the present invention, there is provided a process for the production of the above dry reagent (II) for fibrinogen assay, comprising freeze-drying a mixed liquid consisting essentially of:
 (a) a protein having thrombin activity (component a),
 (b) at least one additive selected from the group consisting of amino acid, a salt thereof and saccharide (component b), and
 (c) water-based medium (component d).

For example, the dry reagent (I) of the present invention can be produced by dissolving the protein having thrombin activity (component a) in the water-based medium (component d), particularly a buffer solution, adding the predetermined amounts of the magnetic particles (component c) and the additive (component b) such as amino acid, a salt thereof or saccharide to form a final solution, then placing the predetermined amount of the final solution in a reaction slide, freezing the placed final solution and freeze-drying the frozen solution.

The above reaction slide used in the above production process is not specially limited if it permits optical monitoring of an increase in the viscosity of the dry reagent as an attenuation of the motion signal of the magnetic particles in fibrinogen measurement. For example, a reaction slide shown in FIGS. 1 and 2 can be used. FIG. 1 shows a plane view of one embodiment of the reaction slide, in which the portion within the a dotted line is an essential portion having an inlet for the final solution to be prepared into the dry reagent for fibrinogen assay and an inlet for an assay sample. FIG. 2 specifically shows the structure of the essential portion. For example, the essential portion is constituted by laminating a transparent polyester plate B on a white polyester plate C and then laminating a transparent polyester plate A on tile transparent polyester plate B. The final solution for the dry reagent for fibrinogen assay is charged through an inlet shown in FIG. 1 and filled in a portion indicated as D. When a reaction slide of this type is used, generally, the final solution is charged in an amount of approximately 20 to 30 $\mu l$.

The structure of the reaction slide of this type is also discussed in detail in FIGS. 11 to 16 of U.S. Pat. No. No. 5,110,727.

The contents and activities of the components of the dry reagent for fibrinogen assay, specified in the present specification, refer to amounts and activities per reaction slide when 25 $\mu l$ of the final solution is charged into such a reaction slide as shown in FIGS. 1 and 2 and freeze-dried, unless otherwise specified.

The water-based medium, preferably a buffer solution, in which the protein having thrombin activity, the magnetic particles and the amino acid or the salt thereof or the saccharide are to be contained, is not specially limited if it has buffer capacity pH 6.0 to pH 8.0. The water-based medium preferably includes a 20 mM HEPES buffer solution (pH 7.35) or a 20 mM phosphate buffer solution (pH 7.4).

Although not specially limited, the method for drying the buffer solution containing the above essential components is preferably a freeze-drying method. When an air drying method is employed, the solubility of tile reagent deteriorates to some extent, and the intensity of motion signal of the magnetic particles tends to be poor.

The above freeze-drying method is not specially limited. The freeze-drying method includes, for example, a general method in which the final solution of the dry reagent for fibrinogen assay is charged into the reaction slide shown in FIG. 1 through the inlet and the reaction slide is instantaneously frozen with dry ice or liquid nitrogen. The method for drying the frozen final solution is not specially limited, either, while it is preferred to linearly increase the temperature of the frozen reaction slide in a vacuum state from $-30°$ C. to room temperature with the lapse of time for 7 to 13 hours.

The dry reagent (I) of the present invention is preferably in the form of a film in which it is formed within the reaction slide.

The dry reagent (II) of the present invention can be produced by dissolving the protein having thrombin activity (component a) in a water-based medium, preferably a buffer solution, adding an additive such as the amino acid, salt thereof or saccharide to prepare a final solution, charging a determined amount of the final solution to a reaction cup, freezing the final solution and drying the frozen final solution.

The method for drying the frozen final solution is not specially limited. The method and conditions for drying the frozen final solution are the same as those described regarding the above dry reagent (I). In this case, however, the contents of the components of the dry reagent (II) for fibrinogen assay, specified in the present specification, refer to amounts per reaction cup and activities when 300 $\mu l$ of the final solution is charged into the reaction cup and freeze-dried, unless otherwise specified.

The assay sample containing fibrinogen to which the dry reagents (I) and (II) of the present invention can be applied is not specially limited, and it includes human whole blood, animal whole blood, human plasma and animal plasma. In particular, the dry reagents (I) and (II) of the present invention are preferably applied to human-derived whole blood and plasma.

Method of Assaying Active Fibrinogen

When the above dry reagent (I) or (II) of the present invention is used, fibrinogen in an assay sample can be measured in a broad concentration range accurately with good reproducibility promptly. In particular, according to the present invention, it has been revealed that the fibrinogen assay can be accurately carried out by optically monitoring the motion signal of the magnetic particles of the above dry reagent (I) and examining the relationship between the change in viscosity and the coagulation.

The fibrinogen assay using the dry reagent (I) of the present invention will be explained hereinafter.

The assay of fibrinogen using the dry reagent (I) of the present invention can be carried out by placing the dry reagent (I) on a reaction holding means, adding a predetermined amount of an assay sample to the dry reagent (I), applying a combination of a vibration magnetic field with a static permanent magnetic field immediately after the above addition, thereby to put the magnetic particles contained in the dry reagent (I) in motion, and optically monitoring the motion signal of the magnetic particles with an optically monitoring apparatus.

For the fibrinogen assay using the dry reagent (I) of the present invention, optically monitoring apparatus in the trade names of CG01 (A & T Corp.) and COAG1 (Wako Pure Chemical Industries, Ltd.) are available.

The fibrinogen assay using the dry reagent (I) of the present invention can be carried out on the basis of a change of the motion signal of the magnetic particles with the lapse of time which change is obtained after an assay sample is added to the reagent (I).

The method for determining the fibrinogen concentration of an assay sample on the basis of a change of the motion signal of the magnetic particles with the lapse of time is not specially limited, or a variety of methods are available. For example, there may be employed a known method using the size of negative slope of the motion signal which the magnetic particles show immediately after an assay sample is added. Besides this method, there may be employed a method utilizing a coagulation time in which one selected point in the motion signal intensity is set at an end point and the time from the addition of an assay sample to the end point is taken as the coagulation time.

The method in which one selected point in the motion signal intensity is set at an end point and the time from the addition of an assay sample to the end point is as follows. A point where the motion signal has attenuated at a predetermined ratio to the peak value of the obtained motion signal of the magnetic particles is set at an end point, and the time from the addition of an assay sample to the end point is taken as a coagulation time. The coagulation time obtained by this method correlates well with the fibrinogen concentration in an assay sample.

The method for assaying fibrinogen in plasma using the coagulation time is not specially limited, either, and it is typically carried out as follows. First, three plasmas having known but different concentrations of fibrinogen are respectively diluted in buffer solutions of the same kind, and the resultant diluted plasma solutions are measured for coagulation times corresponding to individual plasmas by the above described method. A calibration curve is prepared on the basis of the so-obtained results. Then, a plasma is diluted in the same buffer solution as that used above at the same dilution ratio, and the resultant diluted plasma solution is measured for a coagulation time in the same manner as above, and the fibrinogen concentration is determined on the basis of the so-obtained coagulation time by reference to the above-prepared calibration curve. In this case, it is preferred to use a calibration curve of a log-log graph in which X-axis shows fibrinogen concentrations and Y-axis shows coagulation times.

The above buffer solution for diluting an assay sample (e.g., plasma) can be selected from any buffer solutions, while OWREN's buffer is preferred.

According to the present invention, there is provided a method of assaying fibrinogen in an assay sample, comprising:
 (1) bringing the above dry reagent (I) of the present invention and the assay sample to contact with each other,
 (2) monitoring the viscosity of the dry reagent up to an end point which is arbitrarily set at a point where the viscosity value of the dry reagent is 20/19 to 3 times as large as the minimum value of the viscosity thereof,
 (3) measuring a coagulation time which has lapsed from the contact of the dry reagent and the assay sample to the end point, and
 (4) determining an active fibrinogen content in the assay sample on the basis of the coagulation time.

The assay sample to which the assay method of the present invention is applied is preferably human whole blood or plasma, and particularly preferably human plasma.

The end point referred to in the above assay method is any point set where the viscosity of the dry reagent increases to be 20/19 to 3 times as large as the minimum value of the viscosity after an assay sample is added to the dry reagent. In view of reproducibility, it is particularly preferred to set the end point where the viscosity value increases to be 10/7 to 2 times as large as the minimum viscosity value. When tile end point is set where the viscosity is less than 20/19 (about 1.05) times the minimum viscosity value, the sensitivity is low. When it is set where the viscosity is more than 3 times the minimum viscosity value, the assay range is liable to be narrow.

The viscosity change in the dry reagent (I) of the present invention can be monitored by utilizing the magnetic particles contained therein. The method for monitoring the viscosity change is not specially limited. The monitoring is preferably carried out as follows. The dry reagent (I) is placed on a reaction holding means, then a predetermined amount of an assay sample is added to the dry reagent (I), a combination of a vibration magnetic field and a static permanent magnetic field is applied to put the magnetic particles contained in the dry reagent (I) in motion, and the motion signal of the magnetic particles is optically monitored. For the above monitoring, any commercially available apparatus including the foregoing apparatus can be used.

When a commercially available monitoring apparatus is used, a change in the motion signal of the magnetic particles which reversely corresponds to the viscosity change of the dry reagent is obtained as a change with the lapse of time. To explain the present invention in this case, the minimum value of the viscosity is a point where all the components of the dry reagent are dissolved, i.e., where the motion signal of the magnetic particles immediately after the addition of an assay sample shows a peak value. This is further explained by reference to FIG. 4-A. FIG. 4-A shows a typical relationship between the time which has lapsed after the addition of an assay sample (abscissa axis) and the intensity of the motion signal of the magnetic particles (ordinate axis). The intensity of the motion signal indicated by the ordinate axis is in a reverse relation to the viscosity of the reagent. That is, FIG. 4-A shows that as the intensity of the motion signal increases along the ordinate axis, the viscosity decreases.

When an assay sample is added to the dry reagent, the reagent is dissolved in the assay sample, and then the viscosity sharply decreases to reach a minimum value. The point where the viscosity is the minimum is a point where the motion signal of the magnetic particles has a peak value, which peak value is shown as X in FIG. 4-A. The viscosity of the reagent once shows the minimum value and then gradually increases to reach a certain viscosity value at a certain time. When the signal value at this time is taken as Y, the viscosity increase at this time is X/Y times as large as the viscosity in the point X. That is, the time when the attenuation of tile signal intensity relative to the peak value of the motion signal reaches $(X-Y) \times 100/X$ (%) corresponds to a time when the viscosity increase reaches X/Y times as large as the viscosity in the point X. In FIG. 4-A, a point where the signal intensity attenuates from the peak value (X) by 30 % is indicated as Y. In this case, the point Y shows that the viscosity increases to be 10/7 times as large as the viscosity in the point X.

In the assay method of the present invention, any point in the range where the viscosity of the dry reagent increases to be 20/19 to 3 times as large as the viscosity of the minimum value (X), preferably 10/7 to 2 times as large, is set as an end point. And, the period of time from the contact time of the dry reagent and an assay sample to the time of the end point is measured as a coagulation time.

The length of the above coagulation time correlates well with the concentration of fibrinogen in the assay sample.

The method of assaying fibrinogen using the dry reagent (II) of the present invention will be explained hereinafter.

The dry reagent (II) contains no magnetic particles in contrast to the above dry reagent (I) of the present invention. Therefore, the dry reagent (II) can be used similarly to the dry reagent (I) if it is preliminarily dissolved, allowed to contain magnetic particles and dried. However, the dry reagent (II) of the present invention can be used in combination with a steel ball since it contains no magnetic particles, whereby fibrinogen in an assay sample can be accurately determined.

The assay method using the dry reagent (II) will be explained below. The dry reagent (II) consisting essentially of the components a and b is prepared in a reaction cup of KC-10A (supplied by Amelung GmbH, Lemgo). Then, steel ball (supplied by Amelung GmbH, Lemgo) is placed on the dry reagent (II), and an assay sample is added. The time which lapses from the addition of an assay sample to a time when the steel ball begins to move is measured as a coagulation time. The coagulation time obtained by this method correlates well to the concentration of fibrinogen in the assay sample. The method for assaying fibrinogen in plasma by the coagulation time is not specially limited. For example, the assay according to this method is carried out as follows. First, three plasmas having known but different fibrinogen concentrations are respectively diluted in buffer solutions, and the diluted assay sample solutions are measured for coagulation times corresponding to the above three plasmas according to the above assay method. On the basis of the so-obtained results, a calibration curve is prepared. A plasma is diluted in the same buffer solution as those used above at the same dilution ratio. The diluted plasma solution is measured for a coagulation time in the same manner as above, and the fibrinogen concentration is determined on the basis of the so-obtained coagulation time by reference to the above-prepared calibration curve. In this case, it is preferred to use a calibration curve of a log-log graph in which X-axis shows fibrinogen concentrations and Y-axis shows coagulation times.

The above buffer solution for diluting an assay sample can be selected from any buffer solutions as explained concerning the dry reagent (I), while OWREN's buffer is preferred.

In the method of assaying fibrinogen using the dry reagent (I) of the present invention, the most practically excellent is the method in which the dry reagent (I) and an assay sample are brought into contact with each other, the time during which the viscosity increases from the addition of an assay sample to a certain viscosity value (end point) is measured as a coagulation time and the fibrinogen content is determined on the basis of the coagulation time as described above, since the assay can be carried out easily, accurately and promptly.

In addition, studies by the present inventors have revealed that the fibrinogen content in an assay sample can be determined by other modified assay method using the dry reagent (I), since the dry reagent (I) per se is excellent in reactivity, reproducibility and accuracy.

That is, according to the present invention, there are provided modified methods (a-1) to (a-3) of assaying fibrinogen using the dry reagent (I) of the present invention.

(a-1) A method of assaying fibrinogen on the basis of a change of a viscosity with time using the assaying fibrinogen using the dry reagent (I) of the present invention.

(a-1) A method of assaying fibrinogen on the basis of a change of a viscosity with time using the dry reagent (I), the method comprising:
  (i) preliminarily adding assay samples having known fibrinogen concentrations to dry reagents (I), then determining initial viscosity increase rates from a time when each reaction mixture shows a minimum viscosity value to a predetermined time and assay ranges corresponding to the initial viscosity increase rates for determining a concentration of an assay sample, and
  (ii) adding an assay sample having an unknown concentration to the dry reagent (I), measuring the resultant reaction mixture for an initial viscosity increase rate, determining an assay range on the basis of the initial viscosity increase rate, measuring the reaction mixture for a viscosity increase rate in the assay range and determining a fibrinogen content in the assay sample on the basis of the viscosity increase rate.

(a-2) A method of assaying fibrinogen on the basis of a change of a viscosity with time using the dry reagent (I), the method comprising:
  (i) preliminarily adding assay samples having known fibrinogen concentrations to dry reagents (I), then determining viscosity minimum times from the addition of the assay samples to a time when each reaction mixture shows a minimum viscosity and assay ranges corresponding to the viscosity minimum times for determining a concentration of an assay sample, and
  (ii) adding an assay sample having an unknown concentration to the dry reagent (I), measuring the resultant reaction mixture for a viscosity minimum time, determining an assay range on the basis of the viscosity minimum time, measuring the reaction mixture for a viscosity increase rate in the assay range and determining a fibrinogen content in the assay sample on the basis of the viscosity increase rate.

(a-3) A method of assaying fibrinogen on the basis of a change of a viscosity with time using the dry reagent (I), the method comprising:
  (i) preliminarily determining an assay range in a range where the viscosity of the reaction system is 20/19 to 2 times as large as a value of the minimum viscosity, and
  (ii) adding an assay sample having an unknown concentration to the dry reagent (I), measuring the reaction mixture for a viscosity increase rate in the assay range and determining a fibrinogen content in the assay sample on the basis of the viscosity increase rate.

When any one of the above methods (a-1) to (a-3) is employed with the foregoing apparatus such as "CG01" or "COAG1", tile signal waveform shown in FIG. 4-A is converted to a logarithmic signal waveform shown in FIG. 4-B, and the fibrinogen assay is characteristically carried out on the basis of a linear portion of the logarithmic signal waveform. These methods will be explained hereinafter. When the viscosity change in the system is examined by means of a measuring apparatus such as CG01 or COAG1, a signal waveform shown in FIG. 4-A is obtained. Then, a logarithm of tills signal intensity is calculated. The so-obtained waveform is called a logarithmic signal waveform. For example, a logarithmic signal waveform shown in FIG. 4-B is obtained. In FIG. 4-B, the abscissa axis indicates a time after the addition of an assay sample, and the ordinate axis indicates the logarithm of the signal intensity. In the logarithmic signal waveform, it is shown that the smaller the value of logarithm of tile signal intensity is, the higher the viscosity is. That is, in FIG. 4-B, when the reaction system shows the minimum viscosity value, the logarithm of the signal intensity is the largest.

In FIG. 4-B, A, B, C, D, E and F means as follows.
A: Maximum value of the logarithm of the signal intensity.
B: Logarithmic value of tile signal intensity when C second lapses from a time at which reaction system has shown minimum viscosity (Pt).
C: One selected time.
D: Assay range
E: Logarithmic value of the signal intensity at the start point of tile assay range.
F: Logarithmic value of the signal intensity at the end point of the assay range.

The initial viscosity increase rate will be explained hereinafter by reference to FIG. 4-B. In this case, the initial viscosity increase rate is expressed by the following two equations using A and B in the logarithmic signal waveform shown in FIG. 4-B.

Initial viscosity increase conversion coefficient $(\%) = (B/A) \times 100$

Initial viscosity increase rate = 100 initial viscosity increase conversion coefficient (%)

The initial viscosity increase conversion coefficient means that the smaller this coefficient is, the larger tile initial viscosity increase rate is. A shown in FIG. 4-B is the maximum value of logarithmic values of the signal intensity, and this A corresponds to tile logarithmic value of the signal intensity when the reaction system shows the minimum viscosity. B is the logarithmic value of the signal intensity at a time when a selected time C lapses from a time at which the reaction system has shown the minimum viscosity. The time span C shown in FIG. 4-B is not specially limited, and can be freely selected, while C is preferably set at the value of about 12 seconds in view of an improvement in assay accuracy.

In the methods (a-1) to (a-3) of the present invention, fibrinogen can be assayed by measuring the viscosity increase rate in tile assay range. Similarly in FIG. 4-B, the viscosity increase rate in the assay range is expressed by a change amount of logarithmic values of the signal intensity per unit time in the assay range. The viscosity increase rate in the assay range corresponds to tile fibrinogen concentration. That is, the higher the concentration of fibrinogen in blood or plasma is, the larger the viscosity increase rate in the assay range is. In FIG. 4-B, the viscosity increase rate in the assay range is expressed by the following equation.

Viscosity increase rate in the assay range $= (E - F)/D$

The above assay range is preliminarily determined continuously or stepwise so that it corresponds to the initial viscosity increase rate by using assay samples having known concentrations. The continuous determination of the assay range is explained below by reference to FIG. 4-B.

In the continuous determination, first, the signal waveform is obtained by using assay samples having known concentrations. The signal waveform obtained is converted to logarithmic signal waveform. Then, on the basis of this curve (logarithmic signal waveform), a linear region of the curve from a time when the reagent is dissolved, i.e, when the reaction system shows the minimum viscosity to a time when the reaction system shows a constant viscosity after the coagulation has completed and the above initial viscosity increase rate are determined. This linear portion most accurately reflects the fibrinogen concentration. The start point (start time) and end point (finish time) of the so-determined linear portion are plotted in such a manner that these points correspond to the initial viscosity increase rate, and then the assay range within the linear region, i.e., a region between the start point of the linear region and the end point thereof, is determined for each initial viscosity increase rate such that the start point of the assay range comes later as the initial viscosity increase rate decreases or the start point of the assay range comes earlier as the initial viscosity increase rate increases and that the time used for the assay range is longer as the initial viscosity increase rate decreases. In this manner, the viscosity increase rate in the assay range is hardly affected by a noise and can be accurately determined. Continuous lines formed by combining values of the start point (E) of the so-determined assay range and values of end point (F) of the so-determined assay range are preferably curves, and the range between these two continuous lines is taken as the assay range.

To be more specific, when the initial viscosity increase conversion coefficient (%) is 95%, the assay range covers the period of 5.0 seconds from 2.5 seconds after the reaction system shows the minimum viscosity to 7.5 seconds thereafter. When it is 96%, the assay range covers tile period of 7.0 seconds from 7.0 seconds after the reaction system shows the minimum viscosity to 14.0 seconds thereafter. When it is 97%, the assay range covers tile period of 7.5 seconds from 7.5 seconds after the reaction system shows the minimum viscosity to 15.0 seconds thereafter. When it is 98%, the assay range covers the period of 10.0 seconds from 8.0 seconds after the reaction system shows the minimum viscosity to 18.0 seconds thereafter. When it is 99%, the assay range covers the period of 19.0 seconds from 16.0 seconds after the reaction system shows the minimum viscosity to 35.0 seconds thereafter. When it is at least 99.1%, the assay range covers the period of 21.0 seconds from 17.5 seconds after the reaction system shows the minimum viscosity to 38.5 seconds thereafter.

In the stepwise determination, first, the signal waveform is obtained by using assay samples having known concentrations. The signal waveform obtained is converted to logarithmic signal waveform. Then, on the basis of this curve (logarithmic signal waveform), a linear region from a time when the reagent is dissolved, i.e, when the reaction system shows the minimum viscosity, to a time when the reaction finishes so that the reaction system shows a constant viscosity and the initial viscosity increase rate are determined in the same manner as above. The assay range is determined stepwise on the basis of ranges overlapping in the linear region In a manner that the assay range corresponds to the initial viscosity increase rate. The standard on which the initial viscosity increase rate is separated stepwise is properly determined depending upon the corresponding linear region, and it is not constant.

For example, when the above-defined initial viscosity increase conversion coefficient (%) is less than 95%, the assay range is set to cover the period of 5 seconds from 2.5 seconds after the reaction system shows the minimum viscosity to 7.5 seconds thereafter. When the initial viscosity increase conversion coefficient (4) is at least 95% and less than 99.1%, the assay range is set to cover the period of 7.5 seconds from 7.5 seconds after the reaction system shows the minimum viscosity to 15 seconds thereafter. When the above initial viscosity increase conversion coefficient (4) is at least 99.14, the assay range is set to cover the period of 17.5 seconds from 17.5 seconds after the reaction system shows the minimum viscosity to 35 seconds thereafter.

The assay range which corresponds to the initial viscosity increase rate stepwise or continuously is affected by an apparatus and a reagent which are employed. It is therefore required to determine the assay range beforehand by using model plasmas having known fibrinogen concentrations.

For determining the fibrinogen content on the basis of the viscosity increase rate in the assay range, generally, the viscosity increase rates in assay ranges are determined concerning a plurality of assay samples having known fibrinogen concentrations, and calibration curves of viscosity increase rates in assay ranges and fibrinogen concentrations are preliminarily prepared. On the basis of these calibration curves, the fibrinogen content is determined. That is, when an assay sample having an unknown fibrinogen concentration is measured for a viscosity increase rate in the assay range, the fibrinogen concentration can be determined on the basis of the calibration curve.

To explain a specific application example, the upper limit and lower limit of the assay range are handled as a function of the initial viscosity increase rate. That is, the corresponding assay range is determined on the basis of the initial viscosity increase rate. When an assay sample is measured, the initial viscosity increase rate is calculated first, and the assay range is determined on the basis of the obtained value of the initial viscosity increase rate. Further, on the basis of calibration curve preliminarily prepared, the fibrinogen concentration can be determined by calculating the viscosity increase rate in the assay range.

In tile method (a-2) of assaying fibrinogen using the dry reagent (I) on the basis of a change of the viscosity thereof with time, the fibrinogen assay can be carried out by preliminarily adding assay samples having known concentrations to the dry reagents (I), then determining viscosity minimum times from the addition of the assay samples to a time when each reaction mixture shows a minimum viscosity value and assay ranges corresponding to the viscosity minimum times for determining a concentration of an assay sample, then adding an assay sample having an unknown concentration to the dry reagent (I), measuring the resultant reaction mixture for a viscosity minimum time and finally measuring the reaction mixture for a viscosity increase rate in the assay range corresponding to the viscosity minimum time obtained.

The time when the reaction system shows the minimum viscosity and the viscosity increase rate in the assay range are as defined above.

In this method (a-2), the assay range is characteristically determined on the basis of the viscosity minimum time which lapses from the addition of an assay sample to a time when the reaction system shows the minimum viscosity.

That is, the assay range is continuously or stepwise determined in a manner that it corresponds to the viscosity minimum time. The continuous determination of the assay range on the basis of the viscosity minimum time is explained below by reference to FIG. 4-B.

In the above determination, first, the signal waveform is obtained by using assay samples having known concentrations. The signal waveform obtained is converted to a logarithmic signal waveform. Then, on the basis of this curve (logarithmic signal waveform), a linear region of the curve from a time when the reagent is dissolved, i.e, when the reaction system shows the minimum viscosity to a time when the reaction system shows a constant viscosity after the coagulation has completed and the above viscosity minimum time are determined. This linear portion most accurately reflects the fibrinogen concentration. The start point (start time) and end point (finish time) of the so-determined linear portion are plotted in such a manner that these points correspond to the viscosity minimum time, and then the assay range within the linear region, i.e., a region between the start point and the end point, is determined for each viscosity minimum time such that the start point of the assay range comes later as the viscosity minimum time is prolonged or the start point of the assay range comes earlier as the viscosity minimum time is shortened and that the time covered by the assay range is longer as the viscosity minimum time is prolonged. In this manner, the viscosity increase rate in the assay range is hardly affected by a noise and can be accurately determined. Continuous lines formed by combining values of the start point (E) of the so-determined assay ranges and values of the end point (F) of the so-determined assay range are preferably curves, and the range between these two continuous lines is taken as the assay range.

In the stepwise determination, first, the signal waveform is obtained by using assay samples having known concentrations. The signal waveform obtained is converted to a logarithmic signal waveform. Then, on the basis of this curve (logarithmic signal waveform),a linear region from a time when the reagent is dissolved, i.e, when the reaction system shows the minimum viscosity, to a time when the reaction finishes so that the reaction system shows a constant viscosity and the viscosity minimum time are determined in the same manner as above. The assay range is determined stepwise on the basis of ranges overlapping in the linear region in a manner that the assay range corresponds to the viscosity minimum time. The standard on which the viscosity minimum time is separated stepwise is properly determined depending upon the corresponding linear region, and it is not constant.

For example, as shown in Example 12 to be described later, when the viscosity minimum time is less than 5 seconds after the initiation of measurement, the assay range is set to cover the period of 5 seconds from 2.5 seconds after the viscosity minimum time to 7.5 seconds. When the viscosity minimum time is at least 5 seconds and less than 15 seconds after the initiation of measurement, the assay range is set to cover the period of 7.5 seconds from 7.5 seconds after the viscosity minimum time to 15 seconds. When the viscosity minimum time at least 15 seconds after the initiation of measurement, the assay range is set to cover the period of 17.5 seconds from 17.5 seconds after the viscosity minimum time to 35 seconds.

For determining the fibrinogen content on the basis of the viscosity increase rate in the assay range, generally, the viscosity increase rates in assay ranges are determined concerning a plurality of assay samples having known fibrinogen concentrations, and calibration curves of viscosity increase rates in assay ranges and fibrinogen concentrations are preliminarily prepared. On the basis of these calibration curves, the fibrinogen content is determined. That is, when an assay sample having an unknown fibrinogen concentration is measured for a viscosity increase rate in the assay range, the viscosity increase rate can be converted to a fibrinogen concentration on the basis of the calibration curve.

Further, in the method (a-3) of assaying fibrinogen using the dry reagent (I) for fibrinogen assay on the basis of a change of the viscosity thereof with time, the fibrinogen assay is carried out by preliminarily determining an assay range from a range in which the viscosity of a reaction system increases to be 20/19 to 2 times as large as the minimum value of the viscosity, then adding an assay sample having an unknown concentration to the dry reagent (I), and measuring the reaction system for a viscosity increase rate in the assay range.

To explain one embodiment of the above method using the above measuring apparatus for the above blood coagulation dry reagent, there is obtained a change of the motion signal of the magnetic particles with the lapse of time which change is in inverse proportion to the viscosity in a reaction slide. The change of the motion signal shown in FIG. 4-A is obtained. When the signal intensity of the motion signal at which the viscosity is the minimum is taken as X and when the signal intensity at which the viscosity of the reaction system increases to a certain viscosity value is taken as Y, the viscosity at this time increases to be X/Y times as large as the minimum value of the viscosity. That is, the point showing a signal intensity of $Y/X \times 100$ (%) of the signal intensity of the motion signal when the viscosity is minimum corresponds to a point at which the viscosity has increased to be X/Y times as large as the minimum value of the viscosity. For example, the point at which the viscosity of the reaction system has increased to be 20/19 times as large as the minimum viscosity corresponds to a point at which the signal intensity is 95% of the signal intensity of the motion signal of the magnetic particles when the viscosity is the minimum.

In the above method (a-3), two points are set in the range of from a point where the viscosity of the reaction system is 20/19 times as large as the minimum value thereof to a point where the viscosity increases to be 2 times as large as the minimum value, and the range (time) between these two points is determined to be the assay range. It is preferred to set the assay range between 10/9 times and 10/7 times, since reproducibility Is improved. The time between the above two points is not specially limited if it is in the above range, while it is preferably set for at least 2 seconds since the assay accuracy improves.

Meanwhile, when the assay range is set where the viscosity of the reaction system is less than 20/19 times as large as the minimum value thereof, the fibrinogen concentration and the viscosity increase rate in an assay range poorly correlate with each other. When the obtained data is plotted to draw a graph on a squared paper sheet in which the X-axis indicates fibrinogen concentration and the Y-axis indicates viscosity increase rate, the linearity is insufficient. In particular, no fibrinogen in a high concentration cannot at all be determined. When the assay range is set where the viscosity of the reaction system is more than 2 times as large as the minimum value, fibrinogen in a low concentration region cannot be determined, and the measurement in a high concentration region shows a large error. Therefore, the assay range is required to be set in the range where the viscosity of the reaction system is 20/19 to 2 times as large as the minimum value thereof.

For determining the fibrinogen content on the basis of the viscosity increase rate in the assay range, generally, the viscosity increase rates in assay ranges are determined concerning a plurality of assay samples having known fibrinogen concentrations, and calibration curves of viscosity increase rates in assay ranges and fibrinogen concentrations are preliminarily prepared. On the basis of these calibration curves, the fibrinogen content is determined. That is, when an assay sample having an unknown fibrinogen concentration is measured for a viscosity increase rate in the assay range, the viscosity increase rate can be converted to a fibrinogen concentration on the basis of the calibration curve.

The dry reagents (I) and (II) for fibrinogen assay, provided by the present invention, are excellent, since they obviate the restoration of the thrombin reagent and a time for warming an assay sample, and achieve the prompt fibrinogen assay with good reproducibility by only diluting an assay sample in contrast to the fibrinogen assay method using a liquid reagent according to the thrombin time method. The dry reagent (I) and (II) permit broad assay ranges, and unlike a liquid reagent, the dry reagents (I) and (II) substantially obviate procedures of remeasurement of an assay sample by changing the dilution ratio when the assay sample has a fibrinogen concentration outside the assay range. More specifically, conventional reagents only permit the assay in a concentration range of 150 to 800 mg/dl when an assay sample is diluted 20 times, while the dry reagent (I) of the present invention permits the assay in a broad concentration range of 50 to 800 mg/dl when an assay sample is diluted 20 times. The dry reagent (I) of the present invention thus has a characteristic feature in high sensitivity and measurement capability including a low concentration range.

Further, the result of the fibrinogen assay using the dry reagent (I) of tile present invention correlates better to the result of the fibrinogen assay using a liquid reagent than the result of the known dry reagent containing thrombin (U.S. Pat. No. 5,110,727), and the assay using the dry reagent (I) of the present invention can be carried out with improved reproducibility and higher reliability.

As a result of tile development of the dry reagent (I) for fibrinogen assay, provided by the present invention, a measuring apparatus can be decreased in size and further can be handled easily. Therefore, the dry reagent (I) can meet with a bedside urgent test without necessarily requiring an expert.

Moreover, when the dry reagent (II) for fibrinogen assay, provided by the present invention, is used, for example, with an apparatus for fibrinogen assay (trade name, KC-10A, supplied by Amelung GmbH, Lemgo) which generally uses a liquid reagent, the coagulation time and the fibrinogen concentration in plasma correlate to each other well. Therefore, by the use of the dry reagent (II), the fibrinogen assay can be carried out with an apparatus for fibrinogen assay using a liquid reagent without troublesome reagent preparations such as preheating.

The method of assaying a fibrinogen concentration in an assay sample according to the present invention permits a broader concentration range for fibrinogen assay and gives excellent reproducibility as compared with a fibrinogen assay method using a negative slope of the motion signal of magnetic particles. Therefore, the assay method of the present invention obviates procedures of remeasurement of an assay sample by changing the dilution ratio when the assay sample has a fibrinogen concentration outside the assay range as in the fibrinogen assay method using the negative slope of the motion signal of magnetic particles.

Furthermore, the result of the fibrinogen assay using the dry reagents of the present invention correlates very well to the result of the fibrinogen assay using a liquid reagent, and the assay using the dry reagents of the present invention can be carried out with improved reproducibility, higher reliability and higher accuracy.

BRIEF DESCRIPTION OF DRAWINGS

FIG. 4-A shows an end point analysis method for obtaining a coagulation time corresponding to a fibrinogen content by using the dry reagent (I).

FIG. 4-B is a graph showing a logarithmic signal waveform, in which the abscissa axis indicates the lapse of time after the addition of an assay sample and the ordinate axis indicates a logarithmic value of signal intensity.

FIG. 22 shows the correlation between fibrinogen assay values obtained in Example 13 according to the calibration curve shown in FIG. 21 and fibrinogen assay values obtained by a conventional method, in which the abscissa axis indicates the fibrinogen concentration according to the conventional method and the ordinate axis indicates the fibrinogen concentration according to tile method of the present invention.

EXAMPLES

Figure 1:
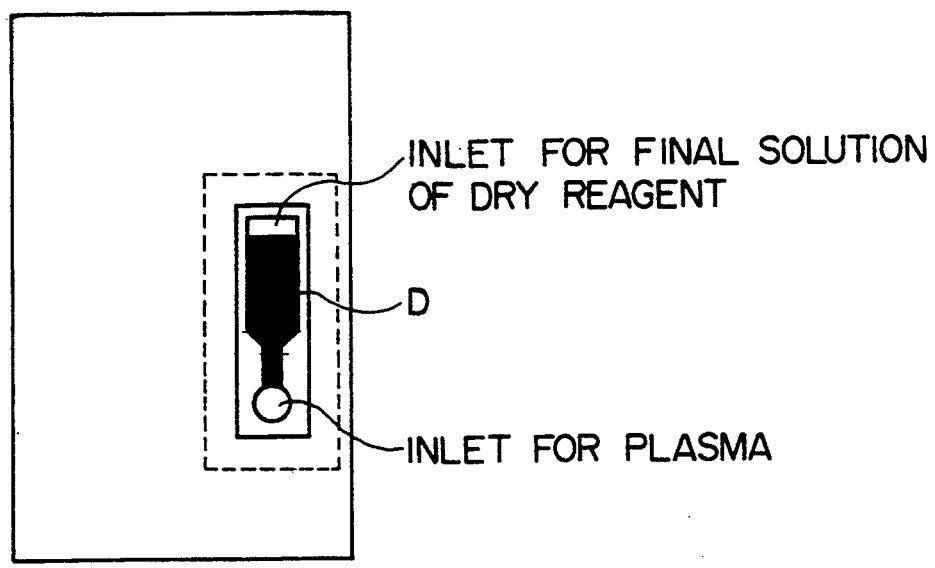
FIG. 1 shows a typical reaction slide for use in the fibrinogen assay using the dry reagent (I) of the present invention in which D indicates a reagent-charging portion.
Figure 2:
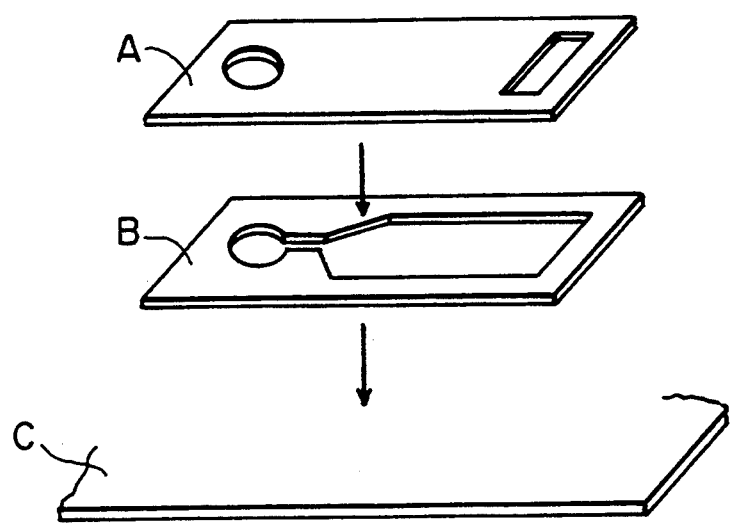
FIG. 2 shows a breakdown of the reaction slide shown in FIG. 1, in which A indicates a transparent resin plate, B indicates a transparent resin plate and C indicates a white resin plate.

The present invention will be explained more in detail by reference to Examples. The present invention, however, is not limited to these Examples.

Example 1 and Comparative Example 1

Comparison of Changes of Motion Signals of Magnetic Particles with the Lapse of Time Depending upon Additives The following six dry reagents were compared concerning changes of motion signals of magnetic particles with the lapse of time by means of a Fibrinogen assaying apparatus (CG01, supplied by A & T Corp.). The compared dry reagents were a thrombin reagent containing glucose (to be abbreviated as "glucose reagent" hereinafter), a thrombin reagent containing sodium L-glutamate monohydrate (to be abbreviated as "sodium glutamate reagent" hereinafter), a thrombin containing bovine serum albumin (to be referred to as "albumin reagent" hereinafter), a thrombin reagent containing Tween 80 (to be abbreviated as "Tween 80 reagent" hereinafter), a thrombin reagent containing PEG6000 (to be abbreviated as "PEG6000 reagent" hereinafter) and a thrombin containing glycerol (to be abbreviated as "glycerol reagent" hereinafter). The above reagents were prepared as follows.

The term "HEPES" in the following preparations of the reagents refers to N-2-hydroxyethylpiperazine-N'-2-ethanesulfonic acid ($C_8H_{18}N_2O_4S$).

Preparation of Glucose Reagent

Pure water was added to a bovine thrombin reagent (supplied by International Reagents Corp.) to prepare 100 U/ml of a thrombin aqueous solution. This thrombin aqueous solution and a 30 mM HEPES (supplied by Dojindo Laboratories) buffer solution (pH 7.35) containing 1.5% glucose (supplied by Wako Pure Chemical Industries, Ltd.) were mixed in a mixing volume ratio of 1:2. Further, ferrosoferric particles (magnetic particles, supplied by Rare Metallic Co., Ltd.) were mixed with the above mixture in such an amount that the final concentration of the ferrosoferric oxide (magnetic particles) was 5 mg/ml, to prepare a final solution for the glucose reagent. The final solution (25 μl) was charged into the same reaction slide as that shown in FIG. 1. The reaction slide was instantaneously frozen and then freeze-dried to obtain a glucose reagent. The above freeze-drying was carried out by linearly increasing the temperature in vacuum from −30° C. to 20° C. with the lapse of 8 hours.

Preparation of Sodium Glutamate Reagent

A sodium glutamate reagent was prepared in the same manner as in tile above preparation of the glucose reagent except that tile 30 mM HEPES buffer solution containing 1.5% (wt/vol.) glucose was replaced with a 30 mM HEPES buffer solution containing 3.0% (wt/vol) sodium L-glutamate monohydrate.

Preparation of Albumin Reagent

An albumin reagent was prepared in the same manner as in the above preparation of the glucose reagent except that the 30 mM HEPES buffer solution containing 1.5% (wt/vol.) glucose was replaced with a 30 mM HEPES buffer solution containing 4.5 mg/ml bovine serum albumin (supplied by Sigma Chemical Company).

Preparation of Tween 80 Reagent

A Tween 80 reagent was prepared in the same manner as in the above preparation of the glucose reagent except that the 30 mM HEPES buffer solution containing 1.5% (wt/vol.) glucose was replaced with a 30 mM HEPES buffer solution containing 0.075% (wt/vol) Tween 80 (nonionic surfactant, supplied by Wako Pure Chemical industries, Ltd.).

Preparation of PEG6000 Reagent

A PEG6000 reagent was prepared in the same manner as in the above preparation of the glucose reagent except that the 30 mM HEPES buffer solution containing 1.5% (wt/vol.) glucose was replaced with a 30 mM HEPES buffer solution containing 1.5% (wt/vol) PEG6000 (polyethylene glycol having an average molecular weight of 6,000, supplied by Koch-Light, Ltd.).

Preparation of Glycerol Reagent

A glycerol reagent was prepared in the same manner as in the above preparation of the glucose reagent except that the 30 mM HEPES buffer solution containing 1.5% (wt/vol.) glucose was replaced with a 30 mM HEPES buffer solution containing 0.75% (wt/vol.) glycerol (supplied by Wako Pure Chemical Industries, Ltd. ).

Comparison of Changes of Motion Signal with the Lapse of Time

Plasma containing 200 mg/dl of fibrinogen was diluted with OWREN's buffer solution (supplied by Sigma Chemical Company) 20 times. Then, each of the above six dry reagents was independently set in a fibrinogen assaying apparatus CG01, and 25 μl of tile above diluted solution was added. Then, the motion signal of magnetic particles from each reagent was optically monitored.

Figure 3:
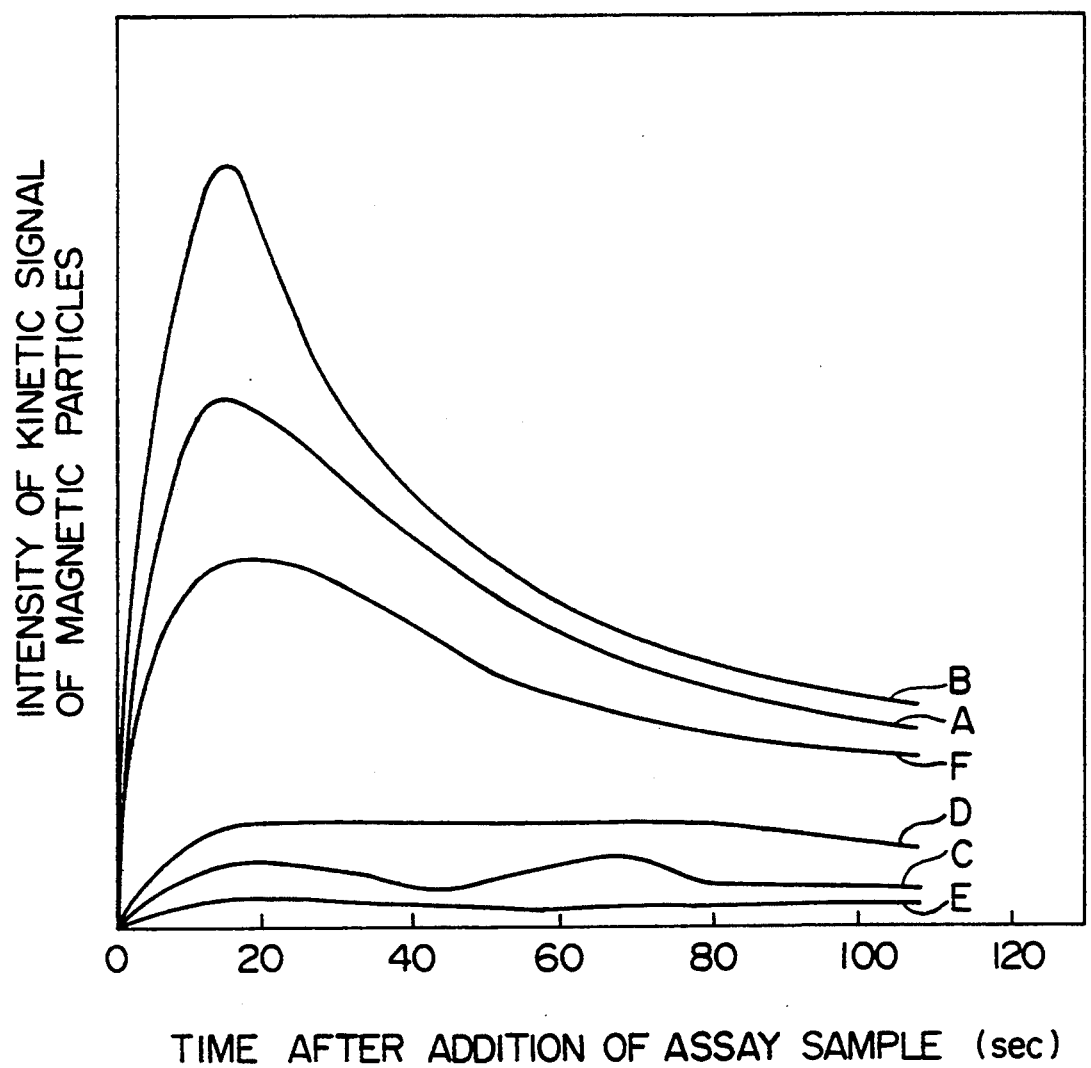
FIG. 3 shows a change of the motion signal intensity of magnetic particles with the lapse of time after the addition of an assay sample to the dry reagent (I).

FIG. 3 shows changes of motion signals of the magnetic particles with the lapse of time after the addition of the diluted solution. In FIG. 3, A indicates a graph obtained from the glucose reagent, B indicates a graph obtained from the sodium glutamate reagent, C indicates a graph obtained from the albumin reagent, D indicates a graph obtained from the Tween 80 reagent, E indicates a graph obtained from the PEG6000 reagent and F indicates a graph obtained from the glycerol reagent.

As is easily understood in FIG. 3, when the glucose reagent, the sodium glutamate reagent and the glycerol reagent were used, the change of motion signal of the magnetic particles with the lapse of time corresponded to an increase in the viscosity of the reagents. The remaining reagents were poor in solubility and showed no correspondence of the motion signal of the magnetic particles to an increase in the viscosity of the reagents.

Comparative Example 2

Dry Reagent Containing No Additive

The following reagents containing no additive (to be abbreviated as "additive-free reagent" hereinafter) were tested with a fibrinogen assaying apparatus (CG01, supplied by A & T Corp.) for changes of motion signals of magnetic particles with the lapse of time. The additive-free reagents were prepared as follows.

Preparation of Additive-free Reagent

Pure water was added to a bovine thrombin reagent (supplied by International Reagents Corp.) to prepare 100 U/ml of a thrombin aqueous solution. This thrombin aqueous solution and a 30 mM HEPES (supplied by Dojindo Laboratories) buffer solution (pH 7.35) were mixed in a mixing volume ratio of 1:2. Further, ferrosoferric oxide (magnetic particles, supplied by Rare Metallic Co., Ltd.) were mixed with the above mixture in such an amount that tile final concentration of the ferrosoferric oxide (magnetic particles) was 5 mg/ml, to prepare a final'solution for the additive-free reagent. An additive-free reagent was prepared from the above final solution in the same manner as in Example 1.

Measurement of Change of Motion Signal with the Lapse of Time

Plasma containing 200 mg/dl of fibrinogen was diluted with OWREN's buffer solution (supplied by Sigma Chemical Company) 20 times. Then the above additive-free reagent was set in a fibrinogen assaying apparatus CG01, and 25 μl of tile above diluted solution was added. Then, the motion signal of magnetic particles from the additive-free reagent was optically monitored°

When tile additive-free reagent was used, the resultant graph was similar to tile graph from the PEG6000 reagent in Comparative Example 1, or no motion signal of the magnetic particles was obtained, and no assay was possible.

Example 2 and Comparative Example 3

Reproducibility of Coagulation Time

The same glucose reagent, sodium glutamate reagent and glycerol reagent as those obtained in Example 1 and Comparative Example 1 and a conventional dry reagent disclosed in U.S. Pat. No. 5,110,727 were tested with a fibrinogen assaying apparatus CG-01 (supplied by A & T Corp.) for reproducibility of coagulation time.

Plasma containing 200 mg/dl of fibrinogen was diluted with OWREN's buffer solution (supplied by Sigma Chemical Company) 20 times. Then one of the above reagents was set in a fibrinogen assaying apparatus CG01. and 25 μl of the above diluted solution was added. Then, the motion signal of magnetic particles from the reagent was optically monitored. These procedures were repeated five times for each reagent. Table 1 shows the results. Table 1 also shows the average values thereof and coefficients of variation values (CV values).

The end point and coagulation time were set as shown in FIG. 4-A. That is, in the graph showing the change of the motion signal of the magnetic particles with the lapse of time, the end point was set at a point where the motion signal attenuated by 30% of the peak value of the motion signal, and the coagulation time was set to cover a period of time from the addition of the assay sample to the end point. Namely, in FIG. 4-A. A indicates the end point, and B indicates the coagulation time.

As shown in Table 1, tile glucose reagent and sodium glutamate reagent, which comes under the present invention, were excellent in reproducibility of the coagulation time. However, the other reagents, i.e., the glycerol reagent and the reagent disclosed in PCT Laid-open Patent Publication No. 504076/1991, showed no reproducibility of the change of motion signal of the magnetic particles with the lapse of time, since these reagents were not uniform in solubility. It has been therefore found that these other reagents showed no reproducibility of the coagulation time.

TABLE 1

| Times | Reagent | | | |
|---|---|---|---|---|
| | Glucose reagent | Sodium glutamate reagent | Glycerol reagent | Reagent described in U.S. Pat. No. 5,110,727 (Unit:see) |
| 1 | 43.0 | 29.0 | 50.0 | 50.0 |
| 2 | 43.5 | 28.5 | 35.0 | 40.0 |
| 3 | 44.0 | 29.5 | 40.0 | 43.0 |
| 4 | 43.5 | 29.0 | 30.0 | 44.0 |
| 5 | 43.0 | 28.5 | 45.5 | 55.0 |
| Average value | 43.4 | 28.9 | 40.1 | 46.4 |
| CV value (%) | 0.96 | 1.45 | 19.92 | 12.98 |

Example 3 and Comparative Example 4

Comparison of Changes of Motion Signal of Magnetic Particles with the Lapse of Time Depending upon Drying Methods The following two fibrinogen assay dry reagents which contained sodium L-glutamate monohydrate as an additive but were produced by different drying methods were compared concerning changes of motion signals of magnetic particles with the lapse of time by means of a fibrinogen assaying apparatus (CG01, supplied by A & T Corp.). The two dry reagents produced by different methods were a dry reagent obtained by freeze-drying after frozen (to be abbreviated as "freeze-dry reagent" hereinafter) and a dry reagent obtained by air-drying (to be abbreviated as "air-dry reagent" hereinafter).

Preparation of Freeze-dry Reagent

A freeze-dry reagent was prepared in the same manner as in the preparation of the sodium glutamate reagent in Example 1.

Preparation of Air-dry Reagent

The same final solution as that described in the preparation of the sodium glutamate reagent in Example 1 was prepared, and charged into the same reaction slide as that shown in FIG. 1. The resultant reaction slide was air-dried in vacuum at 30° C. for 12 hours to obtain an air-dry reagent.

Comparison of Changes of Motion Signal of Magnetic PARTICLES with the Lapse of Time Plasma containing 200 mg/dl of fibrinogen was diluted with an OWREN's buffer solution (supplied by Sigma Chemical Company) 20 times. Then the above dry reagents (I) were respectively set in a fibrinogen assaying apparatus CG01, and 25 μl of the above diluted solution was added. Then, the motion signal of magnetic particles from each reagent was optically monitored.

Figure 5:
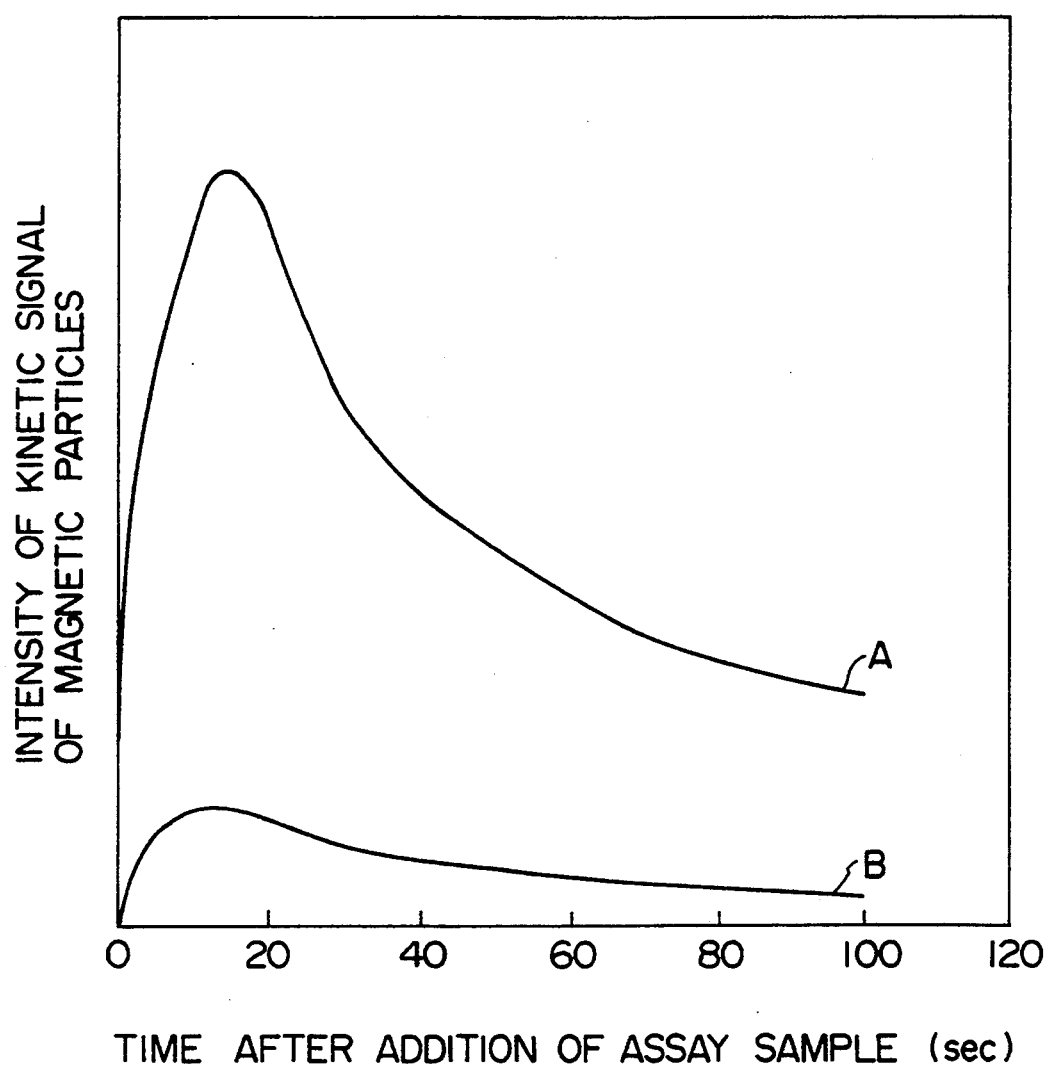
FIG. 5 shows a difference in change of the motion signal intensity of magnetic particles between the dry reagent (I) obtained by freeze-drying and an air-dried reagent.

FIG. 5 shows the changes of motion signals of the magnetic particles with the lapse of time after the addition of the diluted solution.

In FIG. 5, A indicates a graph from the freeze-dry reagent, and B indicates a graph from the air-dry reagent. When the air-dry reagent was used, the motion signal of the magnetic particles was low. When the freeze-dry reagent was used, the motion signal of the magnetic particles was sufficiently high, and showed good reproducibility.

Example 4

Correlation between Fibrinogen Concentration and Coagulation Time

The same freeze-dry reagent (I) as that prepared in Example 3 was tested with a fibrinogen assaying apparatus CG01 (supplied by A & T Corp.) for the correlation between the coagulation time and the fibrinogen concentration.

The end point detection and the coagulation time determination were carried out in the same manner as in Example 2. The correlation between the coagulation time and the fibrinogen concentration was examined as follows. First, a series of human plasma dilution solutions having fibrinogen concentrations of 50 to 800 mg/dl were prepared from human plasma containing 800 mg/dl of fibrinogen and fibrinogen-deficient human plasma (supplied by George King Bio-Medical Inc.). Then, a series of these dilution solutions were respectively diluted with an OWREN's buffer solution 20 times. The above freeze-dry reagent was set at a fibrinogen assaying apparatus CG01, and 25 µl of one of the above diluted solutions was added to determine the coagulation time of the diluted solution in the same manner as in Example 2. In this manner, the coagulation times of all the diluted solutions were determined. The so-obtained data were plotted to draw an X-Y axes logarithmic graph in which the X-axis indicated fibrinogen concentration and the Y axis indicated coagulation time. The correlation was determined on the basis of the linearity of the drawn graph.

Figure 6:
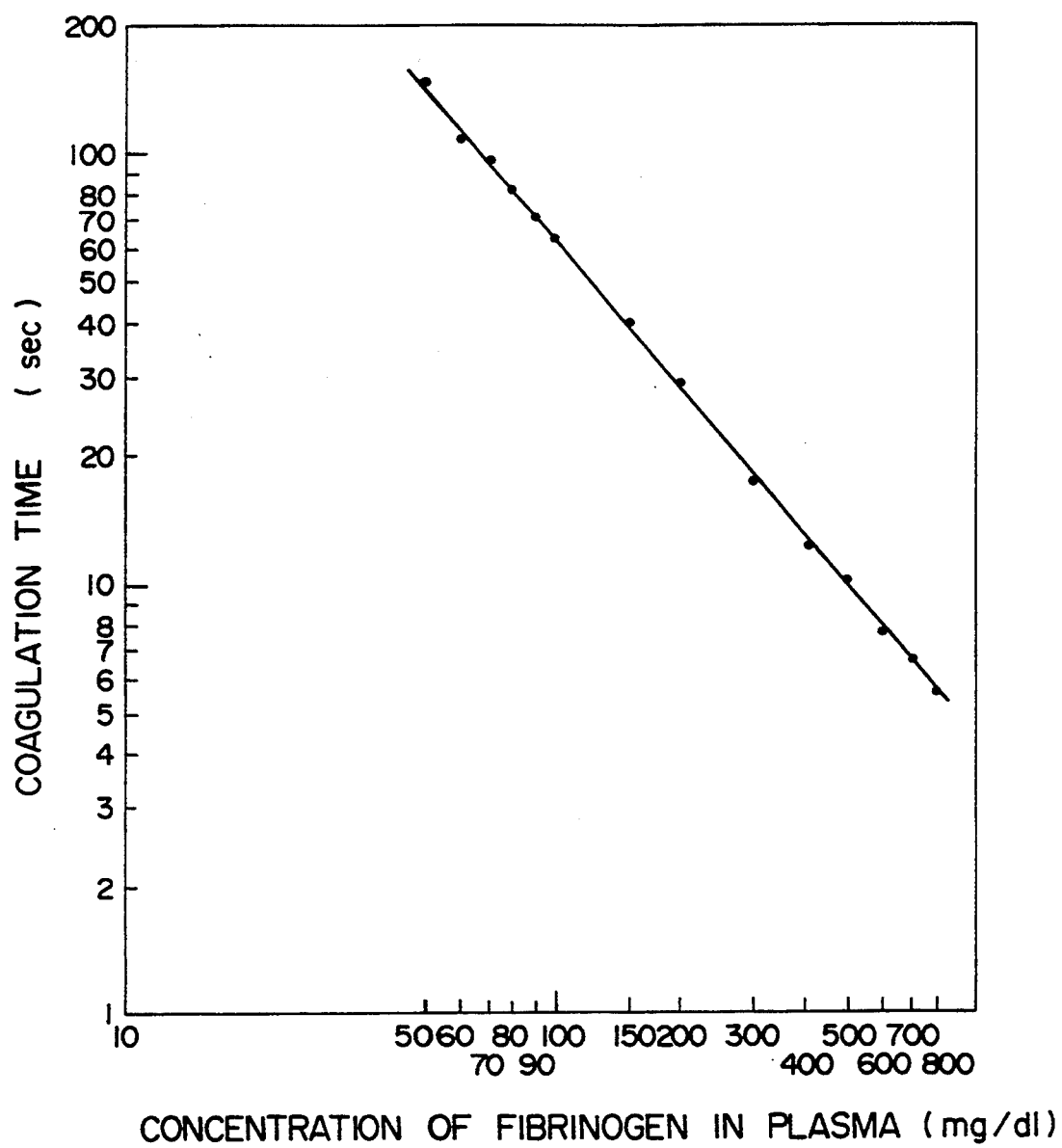
FIG. 6 shows the relationship between the coagulation time and the fibrinogen concentration in plasma, obtained by the end point analysis method shown in FIG. 4-A.

FIG. 6 shows the correlation between the fibrinogen concentration and the coagulation time. As shown in FIG. 6, clearly, the fibrinogen concentration and the coagulation time show a linear relationship, and have the correlation. Further, the result in FIG. 6 shows that fibrinogen can be assayed in the entire concentration range of from 50 to 800 mg/dl when diluted 20 times.

Both when the above plasmas were diluted 10 times and measured for coagulation time and when the above plasmas were diluted 40 times and measured for coagulation time, the resultant coagulation time and the fibrinogen concentrations in plasma showed a linear relationship although the assay range differed.

Example 5

Correlation between Liquid Reagent Method and Dry Reagent Method

The results of fibrinogen assay of 41 human plasma assay samples by a conventional method using a liquid reagent and the results of fibrinogen assay of 41 human plasma assay samples using the dry reagent (I) of the present invention were compared.

In the fibrinogen assay by a conventional method using a liquid reagent, Data-Fi.fibrinogen (supplied by International Reagents Corp.) was tested with a measuring apparatus KC-10A (supplied by Amelung GmbH, Lemgo) according to the instructions attached to Data-Fi.fibrinogen.

In the fibrinogen assay using the dry reagent (I) of the present invention, the same freeze-dry reagent as that prepared in Example 3 was tested with a fibrinogen assaying apparatus CG01 (supplied by A & T Corp.). The end point detection and the coagulation time determination were carried out in the same manner as in Example 2. Human plasma was diluted with an OWREN's buffer solution (supplied by Sigma Chemical Company) 20 times. Then, the above freeze-dry reagent was set at the fibrinogen assaying apparatus CG01, and 25 µl of the above diluted solution was added to determine the coagulation time. The fibrinogen concentration in plasma was determined on the basis of the obtained coagulation time by reference, as a calibration curve, to the graph shown in FIG. 6 referred to in Example 4.

Figure 7:
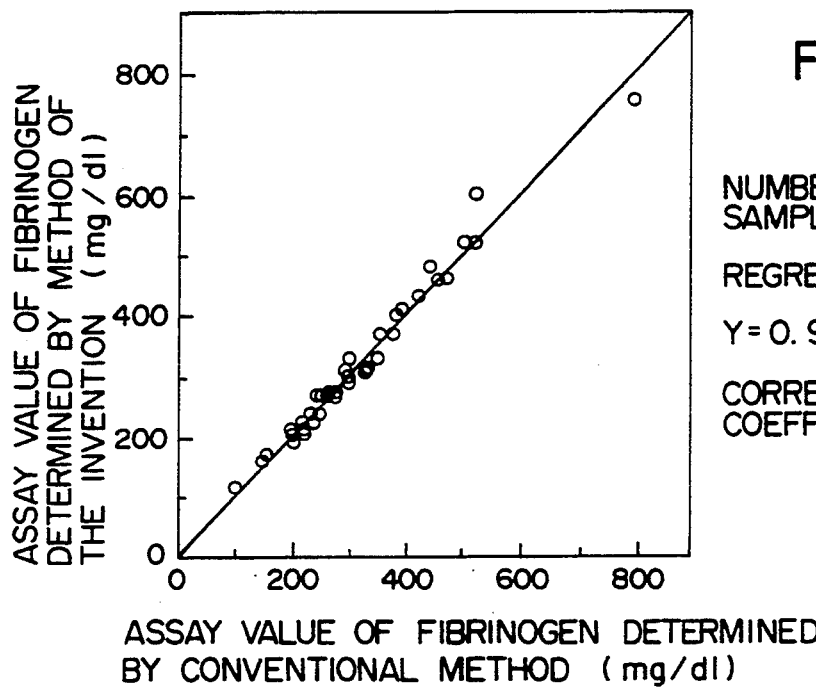
FIG. 7 shows the correlation between fibrinogen assay values obtained by a conventional liquid reagent method and fibrinogen assay values obtained by the assay method using the dry reagent (I) of the present invention.

FIG. 7 shows the correlation between the fibrinogen assay values obtained by the conventional method using the liquid reagent and the fibrinogen assay values obtained by the method of the present invention.

As shown in FIG. 7, clearly, the fibrinogen assay value obtained by the conventional method using the liquid reagent and the fibrinogen assay value obtained by the method of the present invention highly correlate to each other.

Example 6

Correlation between Coagulation Time by Dry Reagent (II) and Fibrinogen Concentration The dry reagent (II) to be used with KC-10A (supplied by Amelung GmbH, Lemgo) was prepared as follows.

Pure water was added to a bovine thrombin reagent (supplied by International Reagents Corp.) to prepare 100 U/ml of a thrombin aqueous solution. This thrombin aqueous solution and a 30 mM HEPES buffer solution (supplied by Dojindo Laboratories, pH 7.35) containing 3.0% sodium L-glutamate monohydrate (supplied by Wako Pure Chemical Industries, Ltd.) were mixed in a mixing volume ratio of 1:2 to prepare a final solution for the dry reagent (II). The final solution (300 µl) was charged into a reaction cup (supplied by Amelung GmbH, Lemgo). The reaction cup was instantaneously frozen with liquid nitrogen and then freeze-dried to obtain a dry reagent (II) for fibrinogen assay. The above freeze-drying was carried out by linearly increasing the temperature in vacuum from −30° C. to 20° C. with the lapse of 8 hours.

The above dry reagent (II) was set at a KC-10A, and then a steel ball (supplied by Amelung GmbH, Lemgo) was placed therein. Then, 300 µl of an assay sample was added, and the time from the addition of the assay sample to a time when the steel ball began to move was measured as a coagulation time.

The correlation between the coagulation time and the fibrinogen concentration was examined as follows. The same six human plasmas having fibrinogen concentrations of 200,300,400,500,600 and 700 mg/dl as those prepared in Example 4 were respectively diluted with an OWREN's buffer solution (supplied by Sigma Chemical Company) 20 times. These diluted solutions were used as assay samples to determine the coagulation time of each diluted solution by the above method. The so-obtained data were plotted to draw an X-Y axes logarithmic graph in which the X-axis indicated fibrinogen concentration and the Y-axis indicated coagulation time. The correlation was determined on the basis of the linearity of the drawn graph.

Figure 8:
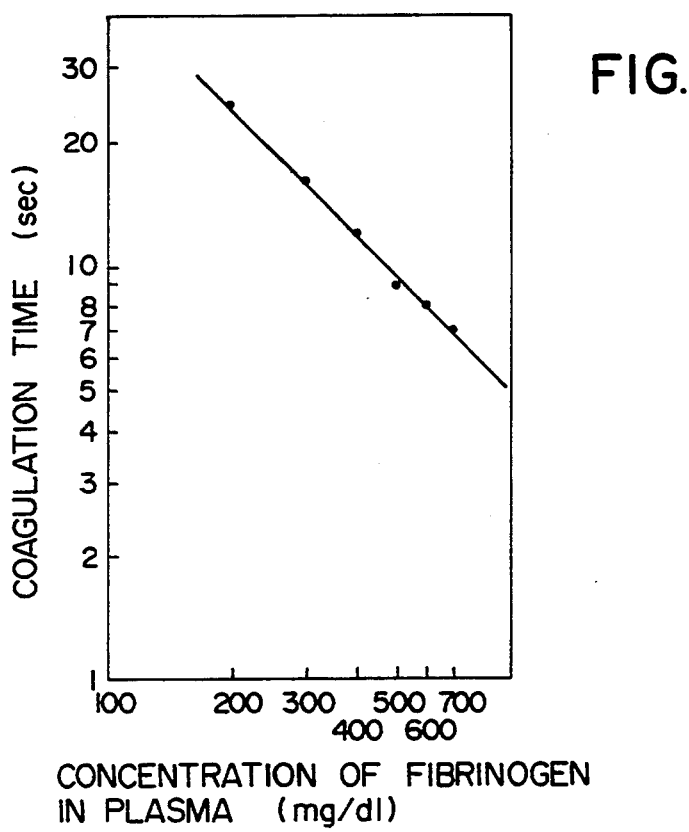
FIG. 8 shows the relationship between the coagulation time obtained by using the dry reagent (II) and the fibrinogen concentration in plasma.

FIG. 8 shows the correlation between the fibrinogen concentration and the coagulation time. As shown in FIG. 8, clearly, the fibrinogen concentration and the coagulation time show a linear relationship and hence, have the correlation. Therefore, when the dry reagent (II) of the present invention is used, fibrinogen can be assayed with a fibrinogen assaying apparatus used with a liquid reagent, without complicated preparations such as preheating.

Example 7

Correlation between Fibrinogen Concentration in Plasma and Coagulation Time when Snake Venom Protein and Human Thrombin are Used as Protein Having Thrombin Activity Two dry reagents (I) for fibrinogen assay were prepared as follows.

Preparation of Snake Venom Protein Reagent

A snake venom protein reagent was prepared in the same manner as in the preparation of a sodium glutamate reagent in Example 1 except that the bovine thrombin reagent was replaced with a freeze-dried product of snake venom protein having thrombin-like activity (Crotalase, supplied by Sigma Chemical Company) and that the freeze-drying was carried out by increasing the temperature linearly from -30 to 30° C in vacuum with the lapse of 13 hours.

Preparation of Human Thrombin Reagent

A human thrombin reagent was prepared in the same manner as in the above preparation of a snake venom reagent except that the freeze-dried product of snake venom protein was replaced with a freeze-dried product of human thrombin (supplied by Sigma Chemical Company).

Correlation between Coagulation Time and Fibrinogen Concentration

CG01 (supplied by A & T Corp.) was used as a fibrinogen assaying apparatus.

The above two dry reagents (I) were tested with a blood coagulation measuring apparatus CG01 for the correlation between the coagulation time and the fibrinogen concentration.

The end point detection and coagulation time determination were as follows. When the snake venom protein reagent was used, a point where the motion signal of the magnetic particles attenuated from the peak value by 10% in FIG. 4-A was set at the end point, and the time from the addition of an assay sample to the end point was taken as the coagulation time. That is, C in FIG. 4-A indicates the end point, and D in FIG. 4-A indicates the coagulation time. The above end point corresponds to a point where the viscosity increases to be 100/90 (about 1.11) times as large as the minimum value of the viscosity.

When the human thrombin reagent was used, a point where the motion signal of the magnetic particles attenuated from tile peak value by 30% in FIG. 4-A was set at the end point, and the time from the addition of an assay sample to the end point was taken as the coagulation time. That is, A in FIG. 4-A indicates the end point, and B in FIG. 4-A indicates the coagulation time. The above end point corresponds to a point where the viscosity increases to be 100/70 (about 1.43) times as large as the minimum value of the viscosity.

The correlation between the coagulation time and the fibrinogen concentration was examined as follows. A series of five dilution solutions of human plasmas having fibrinogen concentrations of 123, 184.5, 246, 369 and 492 mg/dl were prepared from human plasma containing 900 mg/dl of fibrinogen and fibrinogen-deficient human plasma (supplied by George King Bio-Medical, Inc.). Then, a series of these dilution solutions were respectively diluted with an OWREN's buffer solution 15 times. The above freeze-dry reagent was set at a fibrinogen assaying apparatus CG01, and 25 μl of one of the above diluted solutions was added to determine the coagulation time of the diluted solution by the above method. In this manner, the coagulation times of all the diluted solutions were determined. The so-obtained data were plotted to draw an X-Y axes logarithmic graph In which the X-axis indicated fibrinogen concentration and the Y-axis indicated coagulation time. The correlation was determined on the basis of the linearity of the drawn graph, on the basis of which the possibility of fibrinogen assay was determined. Each of the plotted coagulation time values was an average obtained by measuring them five times.

Figure 9:
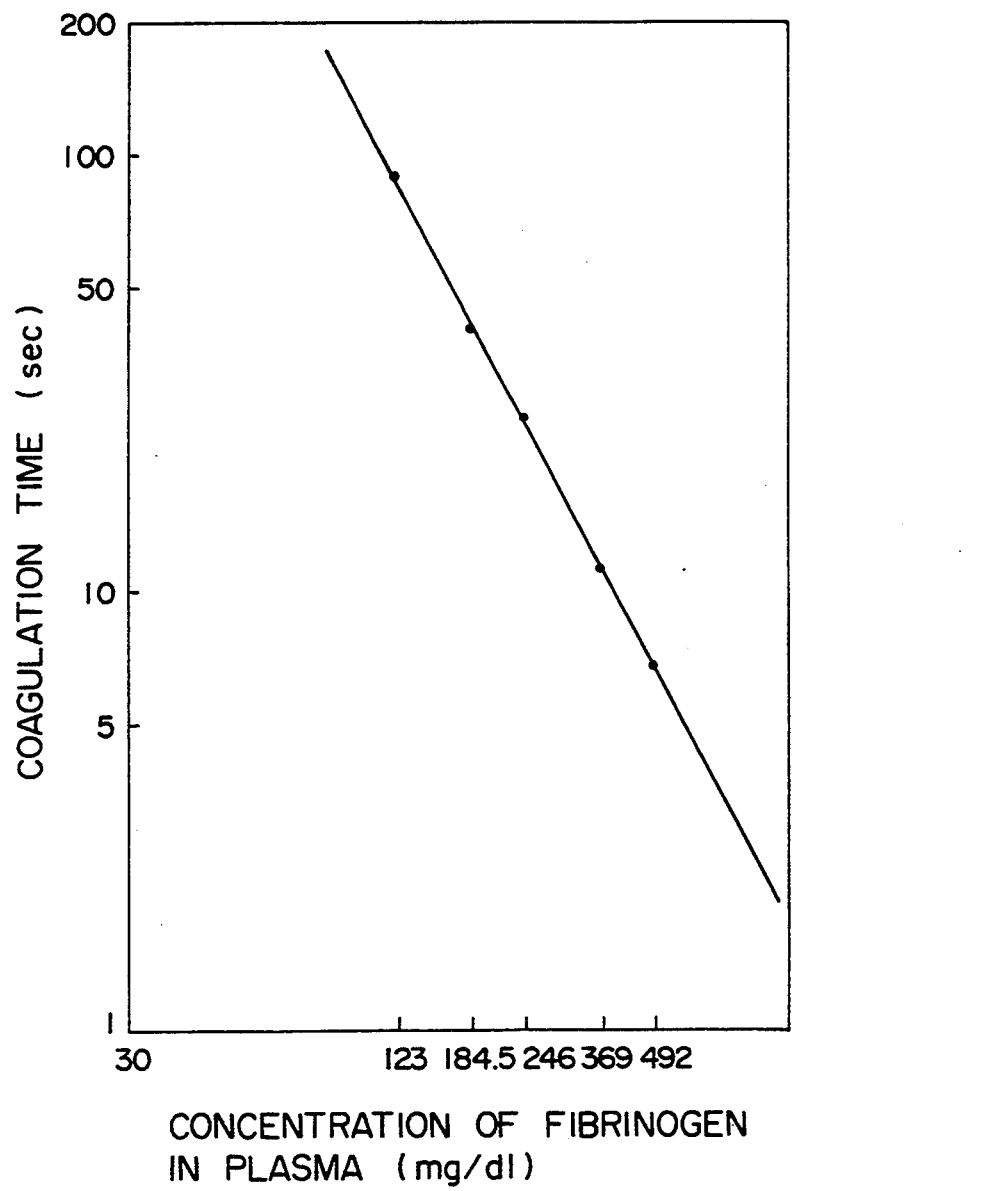
FIG. 9 shows the relationship between the coagulation time obtained by using the dry reagent (I) containing snake venom protein as protein having thrombin activity and the fibrinogen concentration in plasma.
Figure 10:
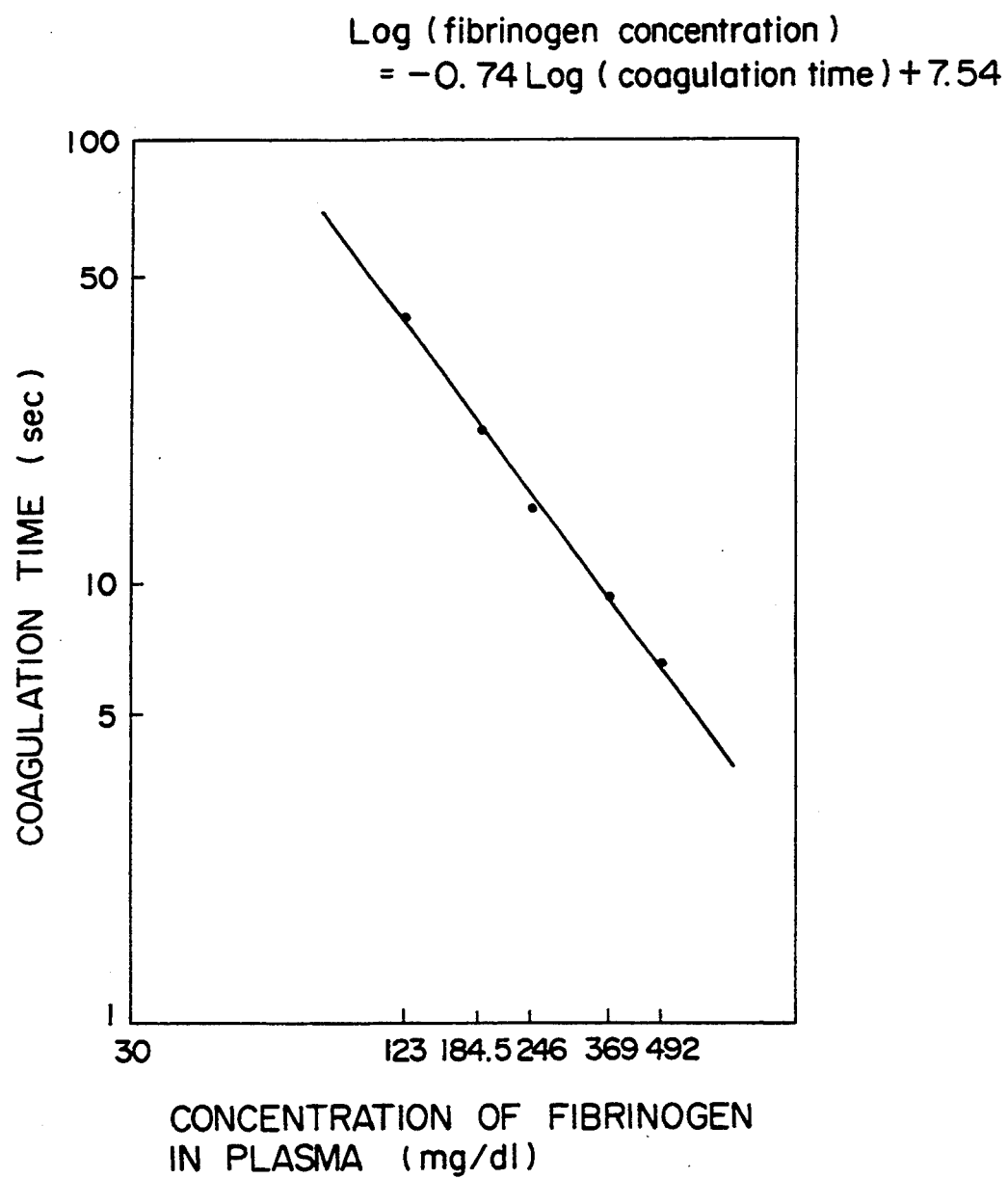
FIG. 10 shows the relationship between the coagulation time obtained by using the dry reagent (I) containing human thrombin as protein having thrombin activity and the fibrinogen concentration in plasma.

FIG. 9 shows the correlation between the fibrinogen concentration and the coagulation time when the snake venom protein reagent was used. FIG. 10 shows the correlation between the fibrinogen concentration and the coagulation time when the human thrombin reagent was used. As shown in FIGS. 9 and 10, clearly, the fibrinogen concentration and the coagulation time show a linear relationship, and have a very good correlation.

That is, it has been found that the above two reagents are capable of assaying fibrinogen.

Example 8

Correlation between Fibrinogen Concentration in Plasma and Coagulation Time when Saccharide is Used as Additive Saccharides such as glucose, fructose and sucrose were selected, and three dry reagents (I) containing these were prepared as follows.

Preparation of Glucose Reagent

A glucose reagent was prepared in the same manner as in the preparation of glucose reagent in Example 1 except that the glucose content in the buffer solution was changed from 1.5% (wt/vol) to 3.0% (wt/vol) and that the freeze-drying was carried out by increasing the temperature linearly from -30° C. to 30° C in vacuum with the lapse of 13 hours.

Preparation of Fructose Reagent

A fructose reagent was prepared in the same manner as in the above preparation of glucose reagent except that the glucose was replaced with fructose (supplied by Wako Pure Chemical Industries, Ltd.).

Preparation of Sucrose Reagent

A sucrose reagent was prepared in the same manner as in the above preparation of glucose reagent except that the glucose was replaced with sucrose (supplied by Wako Pure Chemical Industries, Ltd.).

Correlation between Coagulation Time and Fibrinogen Concentration

The above reagents were examined for the correlation between the coagulation time and fibrinogen concentration in the same manner as in Example 7.

The endpoint of the coagulation time for each reagent was determined as follows. That is, when the sucrose reagent was used, a point where the motion signal of the magnetic particles attenuated from the peak value by 10% in FIG. 4-A (the viscosity increased to be 100/90 times as large as the minimum value of the viscosity) was set at the end point. When the glucose reagent and the fructose reagent were used, a point where the motion signal of tile magnetic particles attenuated from the peak value by 30% in FIG. 4-A (the viscosity increased to be 100/70 times as large as the minimum value of the viscosity) was set at the end point.

Figure 11:
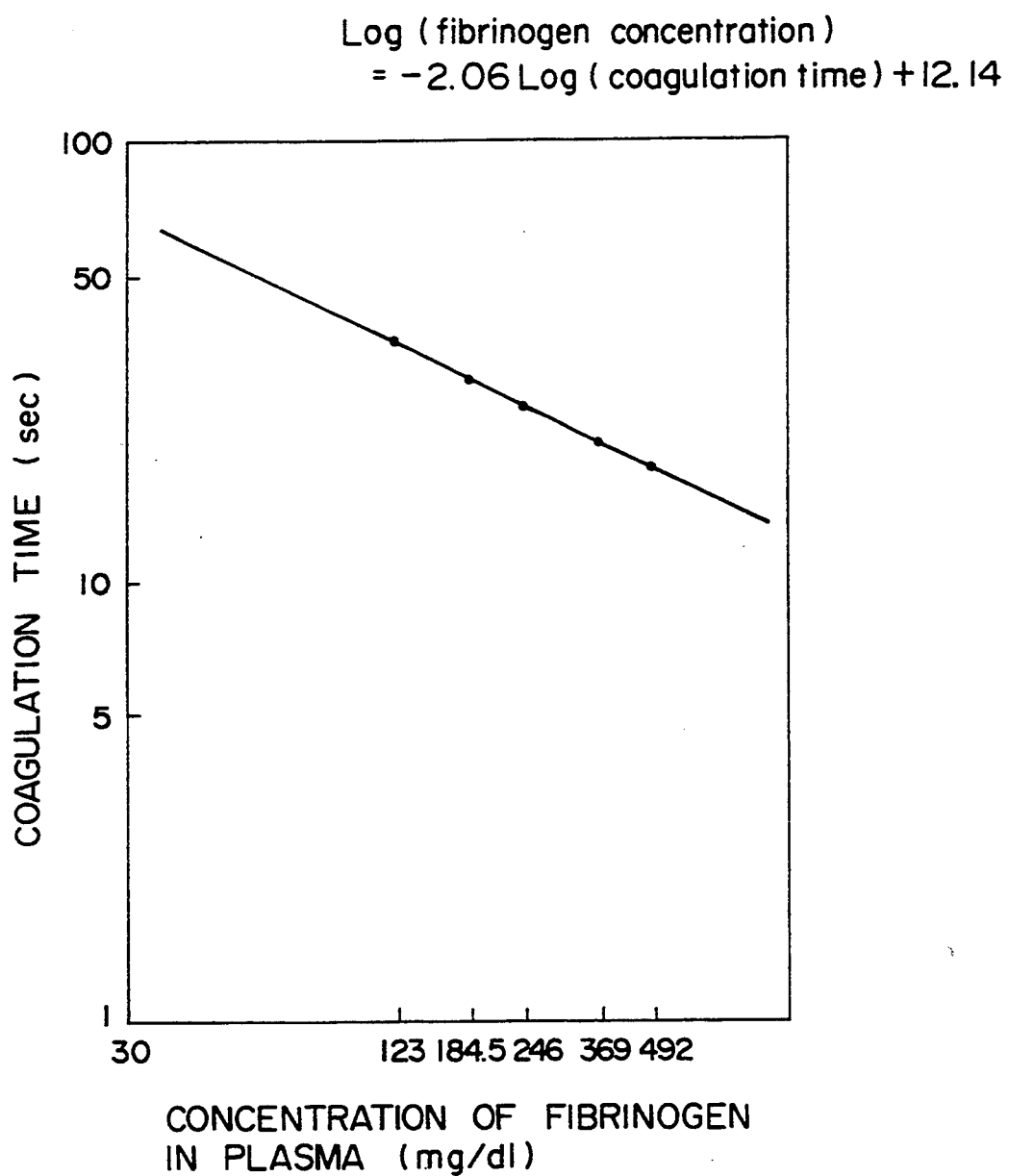
FIG. 11 shows the relationship between the coagulation time obtained by using the dry reagent (I) containing sucrose as an additive and the fibrinogen concentration in plasma.
Figure 12:
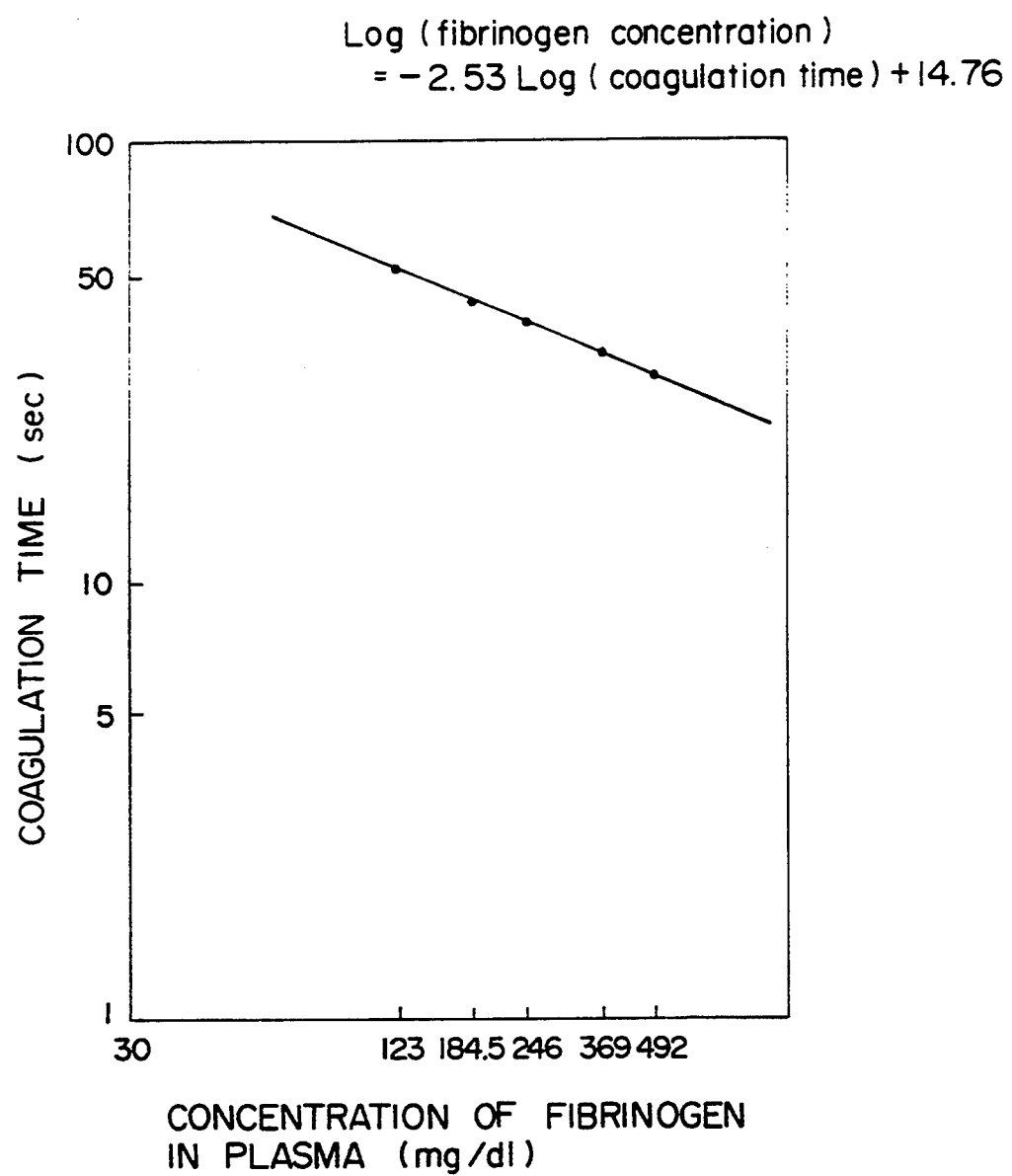
FIG. 12 shows the relationship between the coagulation time obtained by using tile dry reagent (I) containing glucose as an additive and the fibrinogen concentration in plasma.
Figure 13:
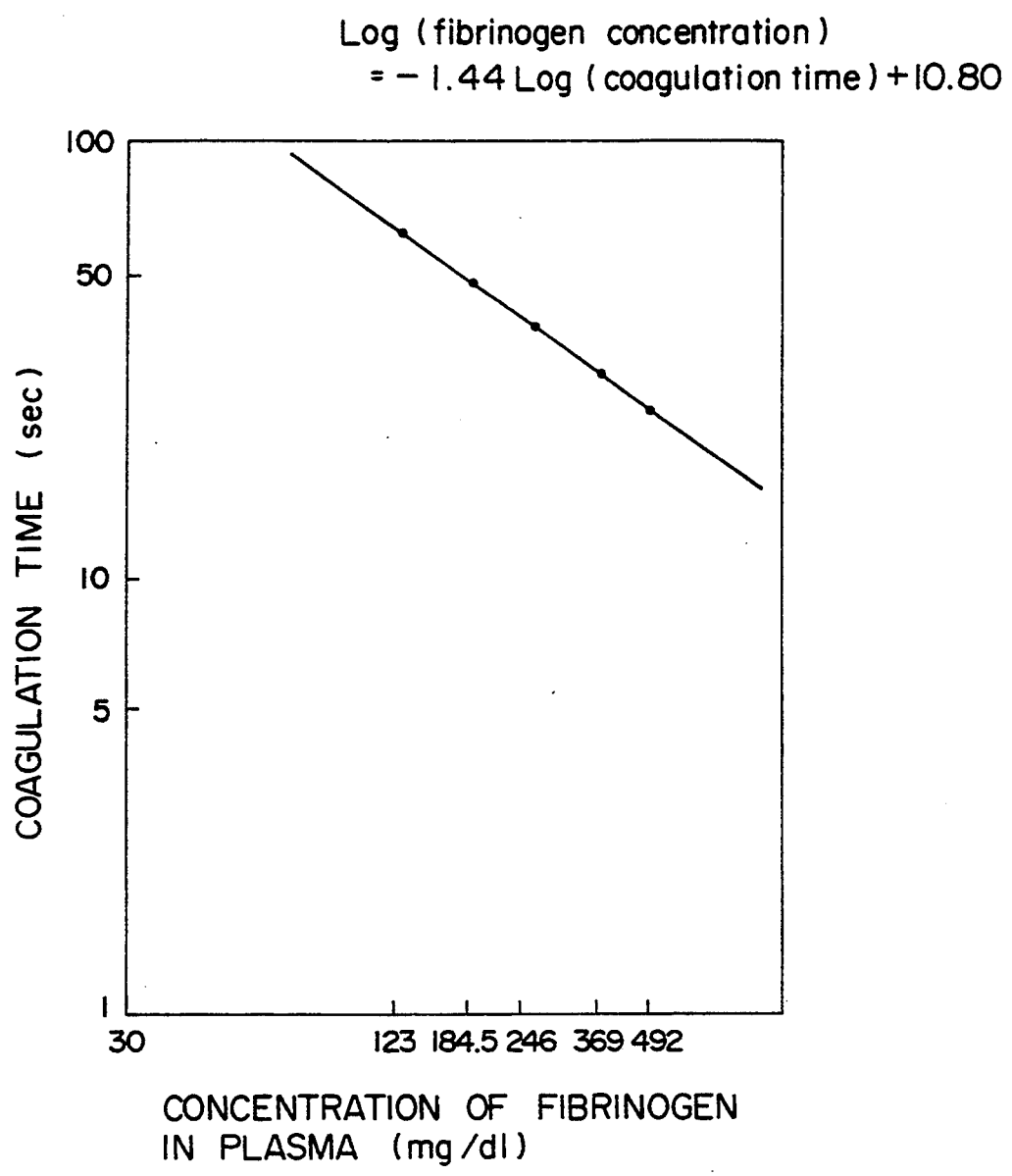
FIG. 13 shows the relationship between the coagulation time obtained by using the dry reagent (I) containing fructose as an additive and the fibrinogen concentration in plasma.

FIG. 11 shows the correlation between the fibrinogen concentration and the coagulation time when the sucrose reagent was used. FIG. 12 shows the correlation between the fibrinogen concentration and the coagulation time when the glucose reagent was used. FIG. 13 shows the correlation between the fibrinogen concentration and the coagulation time when the fructose reagent was used. As shown in FIGS. 11 to 13, the fibrinogen concentration and the coagulation time show a linear relationship, and have a very good correlation although the sensitivity is low as compared with an amino acid reagent (glycine reagent, lysine reagent, sodium aspartate reagent, sodium glutamate reagent, Example 1 and Example 9).

That is, it has been found that the above three reagents are capable of assaying fibrinogen.

Example 9

Correlation between Fibrinogen Concentration in Plasma and Coagulation Time when Amino Acid is Used as Additive L-glycine which was neutral amino acid, L-lysine hydrochloride which was basic amino acid and sodium L-aspartate which was a salt of acidic amino acid were selected. Three dry reagents (I) containing these amino acids were prepared as follows.

Preparation of Glycine Reagent

A glycine reagent was prepared in the same manner as in the preparation of sodium glutamate reagent in Example 1 except that the sodium glutamate was replaced with glycine (supplied by Wako Pure Chemical Industries, Ltd.) and that the freeze-drying was carried out by increasing the temperature linearly from $-30°$ C. to 30° C. in vacuum with the lapse of 13 hours.

Preparation of Lysine Reagent

A lysine reagent was prepared in the same manner as in the above preparation of glycine reagent except that the glycine was replaced with L-lysine hydrochloride (supplied by Wako Pure Chemical Industries, Ltd.).

Preparation of Sodium Aspartate Reagent

A sodium aspartate reagent was prepared in the same manner as in the above preparation of glycine reagent except that the glycine was replaced with sodium L-aspartate (supplied by Wako Pure Chemical Industries, Ltd.).

The above reagents were examined for the correlation between the coagulation time and fibrinogen concentration in the same manner as in Example 7.

The endpoint of the coagulation time for each reagent was determined as follows. That is, when the lysine reagent was used, a point where the motion signal of the magnetic particles attenuated from the peak value by 10% in FIG. 4-A (the viscosity increased to be 100/90 times as large tile minimum value of the viscosity) was set at the end point. When the glycine reagent and the sodium aspartate reagent were used, a point where the motion signal of the magnetic particles attenuated from the peak value by 30% in FIG. 4-A (the viscosity increased to be 100/70 times as large as the minimum value of the viscosity) was set at the end point.

Figure 14:
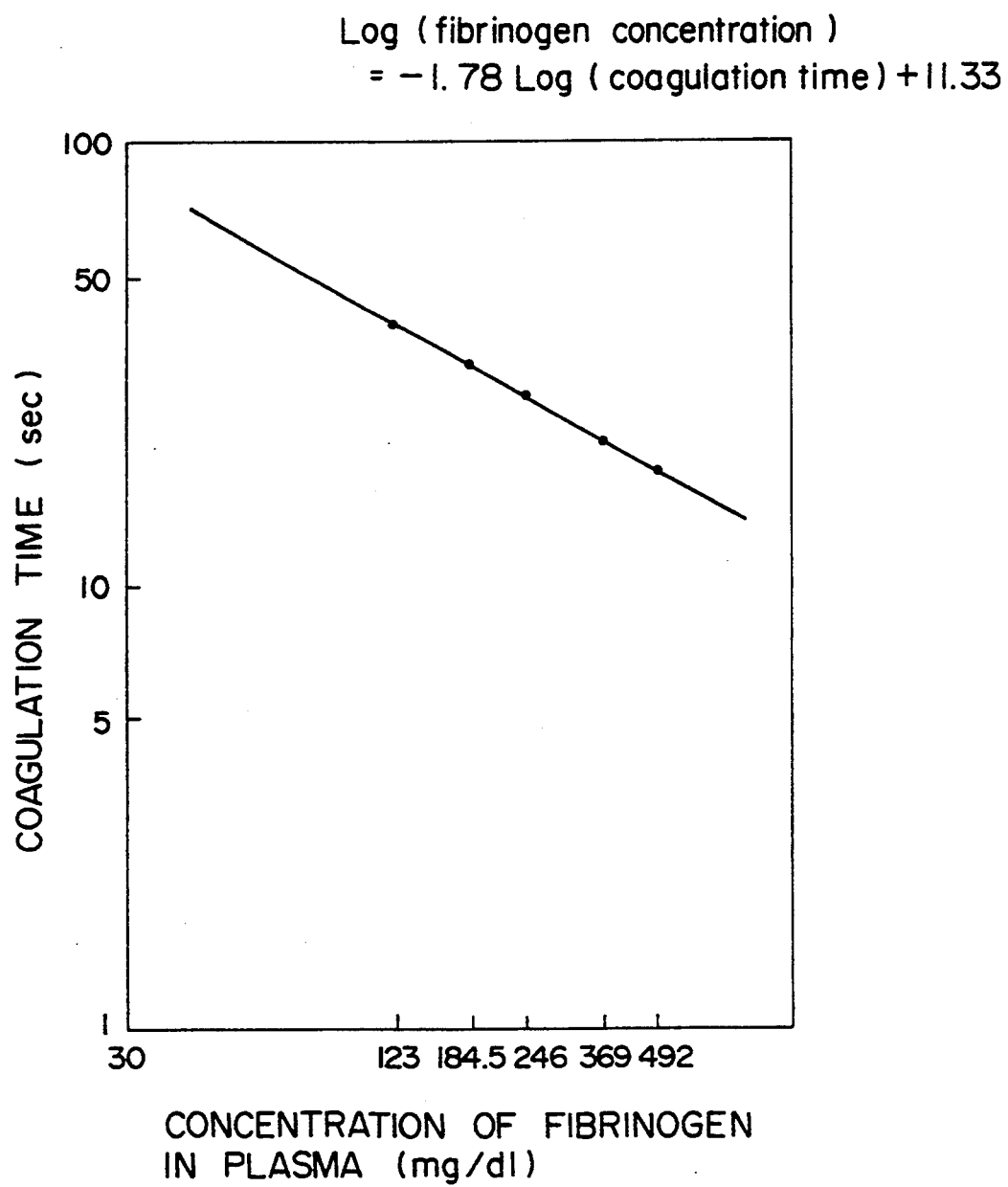
FIG. 14 shows the relationship between the coagulation time obtained by using the dry reagent (I) containing L-lysine chlorate as an additive and the fibrinogen concentration in plasma.
Figure 15:
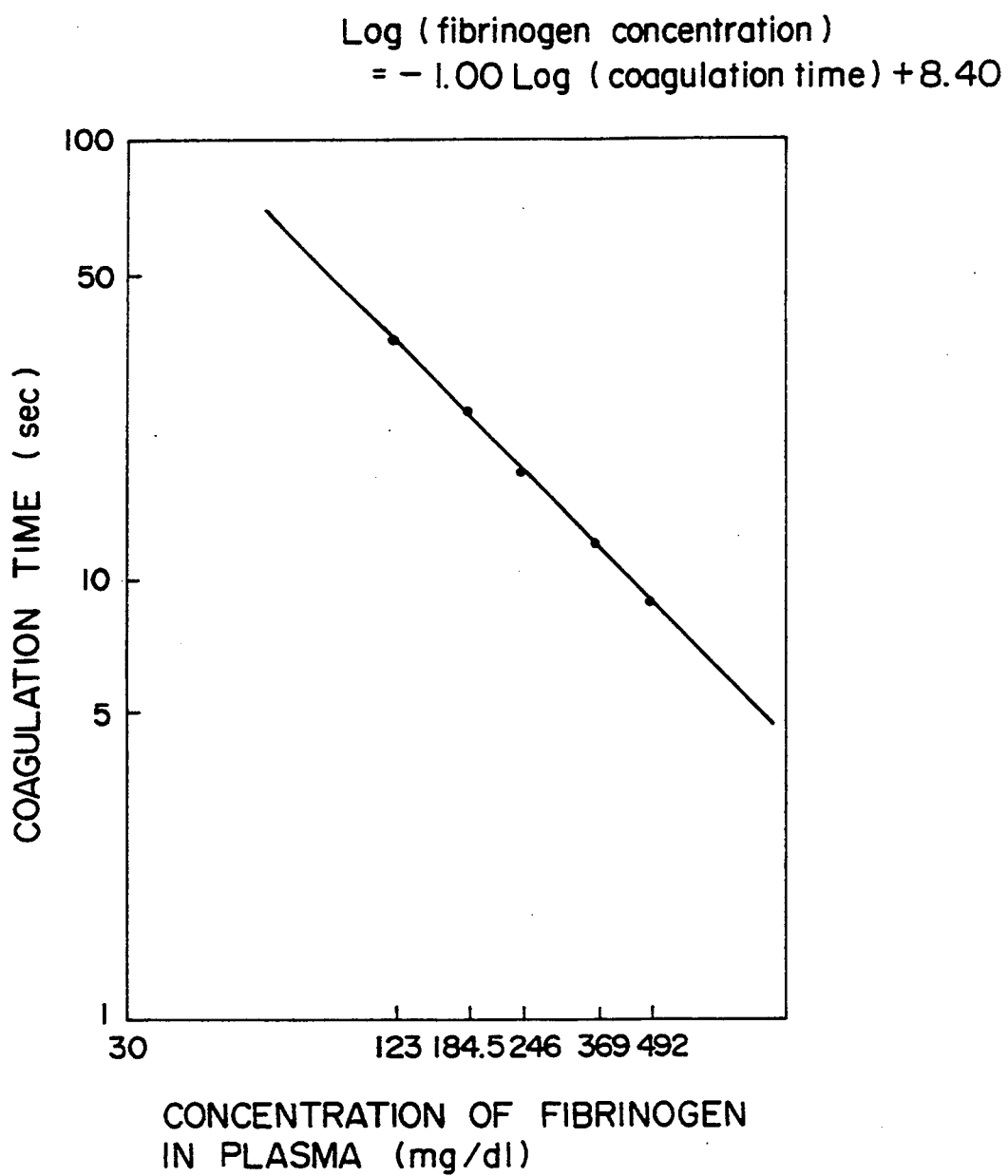
FIG. 15 shows the relationship between the coagulation time obtained by using the dry reagent (I) containing glycine as an additive and the fibrinogen concentration in plasma.
Figure 16:
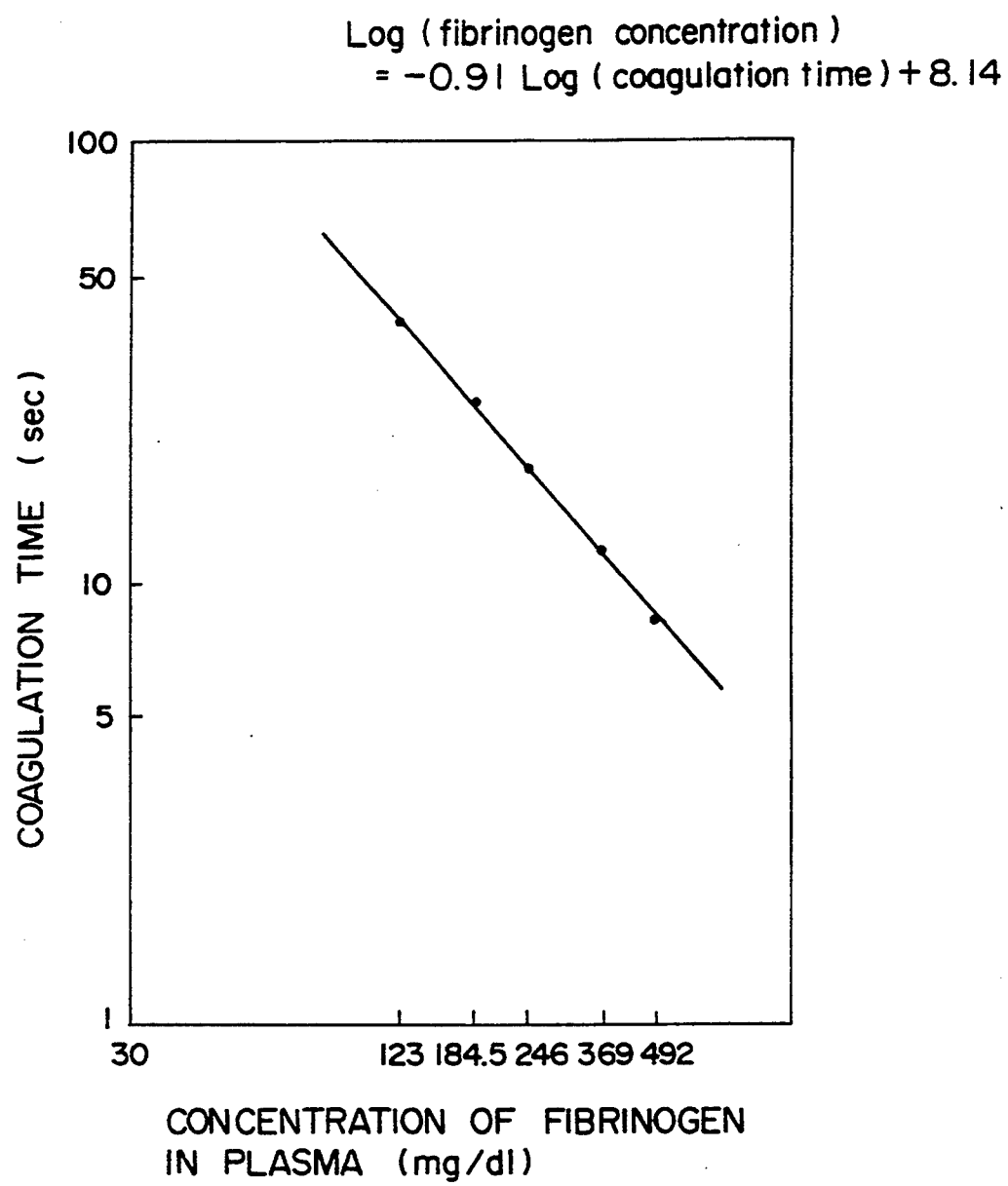
FIG. 16 shows the relationship between the coagulation time obtained by using the dry reagent (I) containing sodium aspartate as an additive and the fibrinogen concentration in plasma.

FIG. 14 shows the correlation between the fibrinogen concentration and the coagulation time when the lysine reagent was used. FIG. 15 shows the correlation between the fibrinogen concentration and the coagulation time when the glycine reagent was used. FIG. 16 shows the correlation between the fibrinogen concentration and the coagulation time when the sodium aspartate reagent was used. As shown in FIGS. 14 to 16, the fibrinogen concentration and the coagulation time show a linear relationship, and have a very good correlation.

That is, it has been found that the above three reagents are capable of assaying fibrinogen.

Example 10

Comparison of Reagents Containing Amino Acids as Additive Concerning Reproducibility Plasma containing 246 mg/dl of fibrinogen was diluted with an OWREN's buffer solution 15 times, and the resultant diluted solution was added to a variety of amino acid reagents to determine a coagulation time for each reagent. These procedures were repeated five times for each reagent, and coefficients of variation values (CV values) were calculated.

The above amino acid reagents were the same as those prepared in the following Examples.
Sodium glutamate reagent: Example 1
Sodium aspartate reagent: Example 9
Glycine reagent: Example 9
Lysine reagent: Example 9
Table 2 shows the results.
Table 2 clearly shows that the reproducibility of measured values when acidic amino acid is used is excellent over that when other amino acids are used.

TABLE 2

| | Amino acid type | | | |
|---|---|---|---|---|
| | Acidic amino acid | | Neutral amino acid reagent | Basic amino acid |
| | Sodium glutamate reagent | sodium aspartate reagent | Glycine reagent | Lysine reagent |
| 1 | 21.4 | 18.1 | 16.1 | 26.0 |
| 2 | 21.3 | 18.9 | 18.3 | 28.5 |
| 3 | 21.2 | 17.9 | 17.9 | 25.5 |
| 4 | 21.5 | 17.9 | 17.2 | 26.5 |
| 5 | 21.0 | 18.5 | 16.3 | 25.5 |
| Average value | 21.3 | 18.3 | 17.2 | 26.4 |
| CV value (%) | 0.90 | 2.37 | 5.60 | 4.72 |

Example 11

Correlation between Fibrinogen Concentration and Coagulation Time when the End Point is Changed The same sodium glutamate reagent as that used in Example 1 was used as a dry reagent (I) and tested with a fibrinogen assay apparatus CG01 (supplied by A & T Corp.) for the correlation between the fibrinogen concentration in an assay sample and the coagulation time when end points were set where the attenuation ratio of motion signal of the magnetic particles to the peak value was changed.

End points were set where the motion signal of the magnetic particles attenuated from the peak value by 10%, 20%, 30% and 40%, and the time from the addition of an assay sample to each end point was taken as a coagulation time. These end points correspond to points where the viscosity increases to be 100/90 (about 1.1) times, 100/80 (1.25) times, 100/70 (about 1.43) times and 100/60 (about 1.67) times as large as the minimum value of the viscosity.

The correlation between the fibrinogen concentration and the coagulation time was examined as follows. A series of dilution solutions of human plasmas having fibrinogen concentrations of 100 to 600 mg/dl were prepared from human plasma containing 600 mg/dl of fibrinogen and fibrinogen-deficient human plasma (supplied by George King Bio-Medical, Inc.). Then, a series of these dilution solutions were respectively diluted with an OWREN buffer solution 20 times. The above freeze-dry reagent was set at a fibrinogen assaying apparatus CG01, and 25 µl of one of the above diluted solutions was added to determine the coagulation time of the diluted solution by the above method. In this manner, the coagulation times of all the diluted solutions were determined. The so-obtained data were plotted to draw an X-Y axes logarithmic graph in which the X-axis indicated fibrinogen concentration and the Y-axis indicated coagulation time. The correlation was determined on the basis of the linearity of the drawn graph.

Figure 17:
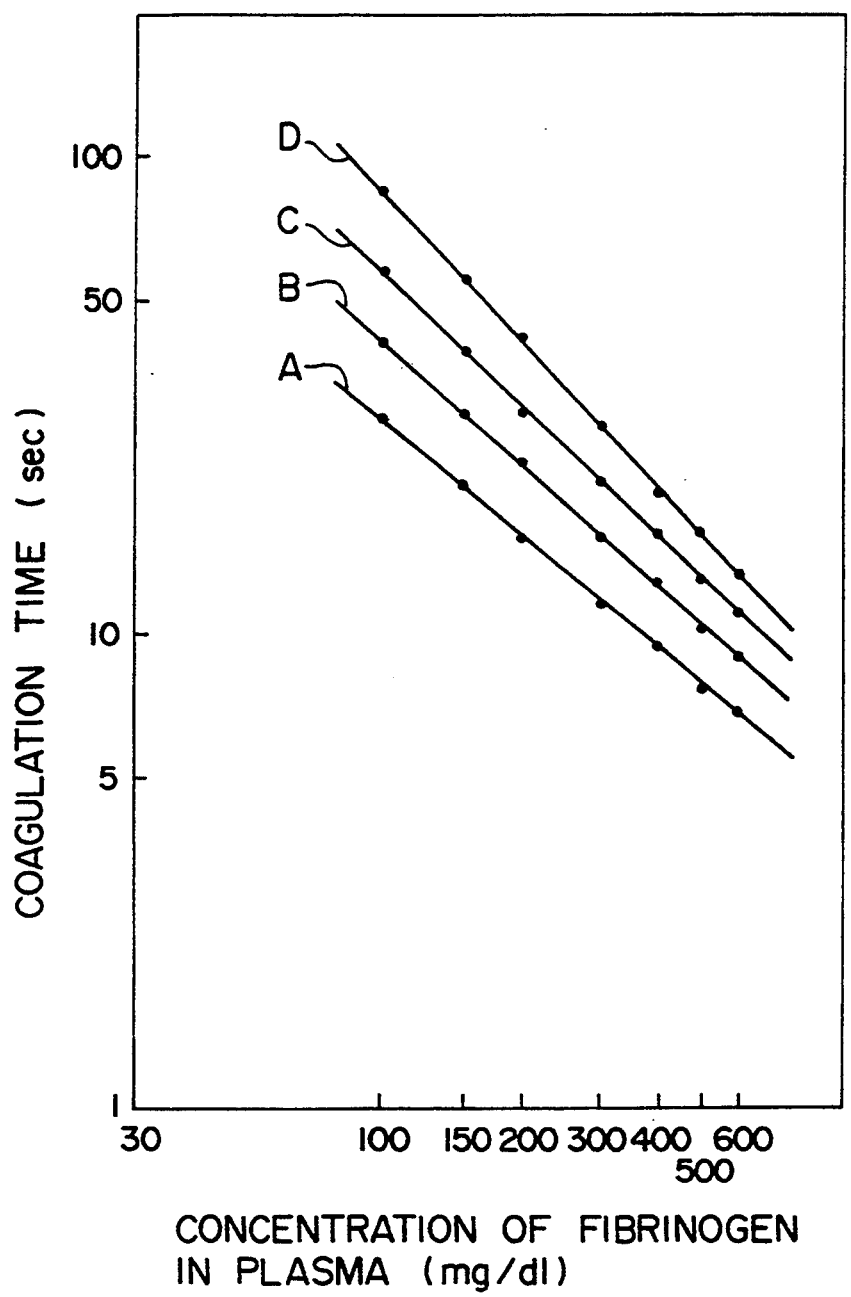
FIG. 17 shows the correlation between the coagulation time obtained when end points are set by changing the ratio of attenuation to the peak value of the motion signal of magnetic particles and the fibrinogen concentration.

FIG. 17 shows the correlation between the fibrinogen concentration and the coagulation time. In FIG. 17, A indicates a graph showing the correlation between the coagulation time and the fibrinogen concentration when the motion signal of the magnetic particles attenuated from its peak value by 10%, B indicates a graph showing the same when the motion signal of the magnetic particles attenuated from its peak value by 20%, C indicates a graph showing the same when the motion signal of the magnetic particles attenuated from its peak value by 30%, and D indicates a graph showing the same when, the motion signal of the magnetic particles attenuated from its peak value by 40

As shown in FIG. 17, when the end point is set by changing tile attenuation ratio to the peak value of motion signal of the magnetic particles within the viscosity change range defined in the present invention, the coagulation time and the fibrinogen concentration in an assay sample well correlates to each other.

Comparative Example 5

Correlation between Conventional Negative Slope Method and the Fibrinogen Concentration The same sodium glutamate reagent as that used in Example 1 was used as a dry reagent (I) and tested with a fibrinogen assay apparatus CG01 (supplied by A & T Corp.) for the correlation between the negative slope and the fibrinogen concentration.

Figure 18:
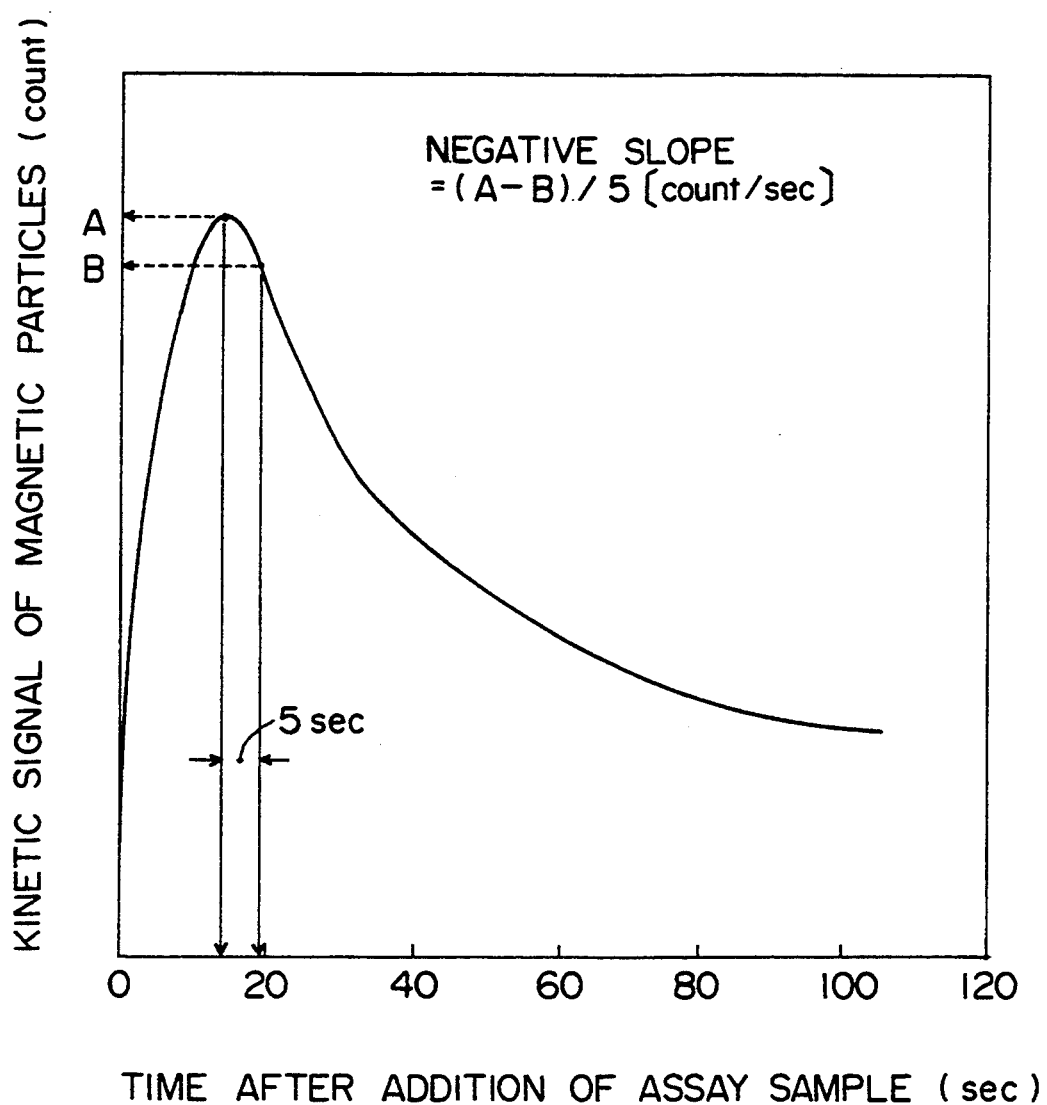
FIG. 18 shows the method for calculation of negative slope of the motion signal of magnetic particles.

The negative slope was measured as follows. First, the peak value of the motion signal was recorded (A in FIG. 18). Then, the value of the signal intensity at a time when 5 seconds lapsed since the motion signal had reached the peak value was recorded (F in FIG. 18), and a change amount of the motion signal per second was calculated as a negative slope on the basis of the above two motion signal values. That is, the range for measuring the negative slope in this Comparative Example covered the period of 5 seconds after the motion signal of the magnetic particles reached the peak. When expressed using symbols in FIG. 18, the negative slope is $(A-B)/5$ [count/sec].

The correlation between the negative slope and the fibrinogen concentration was examined as follows. A series of dilution solutions of human plasmas having fibrinogen concentrations of 50 to 800 mg/dl were prepared from human plasma containing 800 mg/dl of fibrinogen and fibrinogen-deficient human plasma (supplied by George King Bio-Medical Inc.). Then, a series of these dilution solutions were respectively diluted with an OWREN buffer solution 20 times. The above freeze-dry reagent was set at a fibrinogen assaying apparatus CG01, and 25 µl of one of the above diluted solutions was added to determine the coagulation time of the diluted solution by the above method. In this manner, the coagulation times of all the diluted solutions were determined. The so-obtained data were plotted to draw a graph in which the X-axis indicated fibrinogen concentration and the Y-axis indicated the size of the negative slope. The correlation was determined on the basis of the linearity of the drawn graph.

Figure 19:
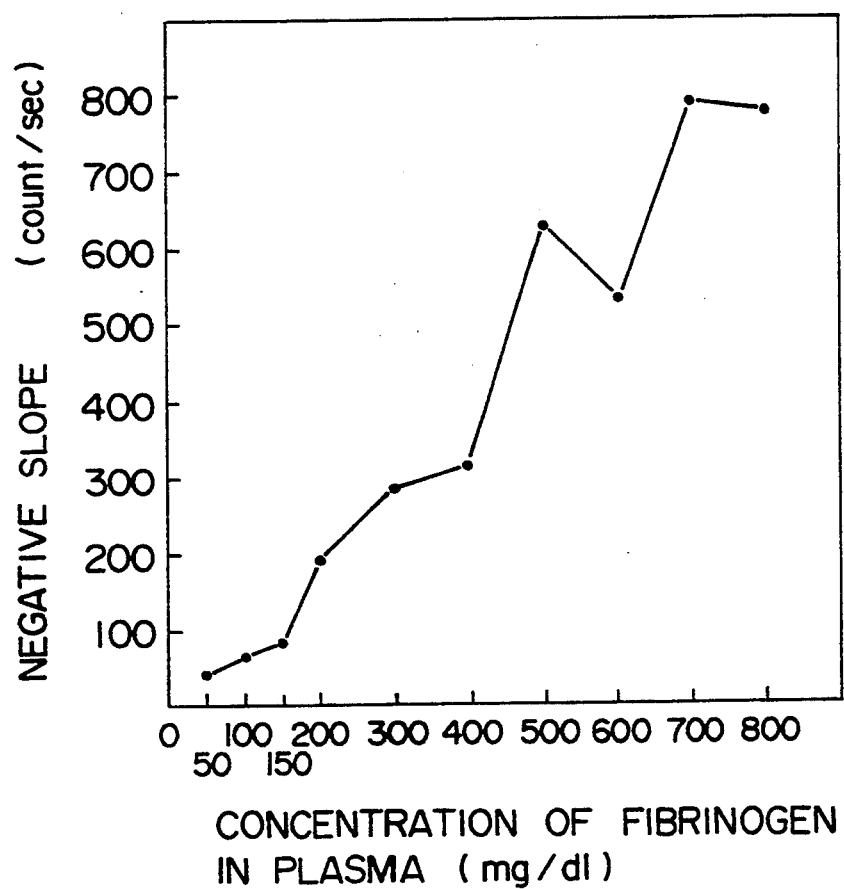
FIG. 19 shows the correlation between the negative slope obtained by the method shown in FIG. 18 and the fibrinogen concentration in plasma.

FIG. 19 shows the correlation between the fibrinogen in the assay sample and the negative slope. As shown in FIG. 19, as the fibrinogen concentration in the assay sample increased, the negative slope became greater, while such a linearity as that shown in Examples 4 and 12 was not obtained. It has been therefore found actually difficult to assay the fibrinogen concentration in an assay sample using the negative slope of motion signal of the magnetic particles.

Comparative Example 6

Correlation between the Fibrinogen Concentration and the Coagulation when the End Point is Changed The same sodium glutamate reagent as that used in Example 1 was used as a dry reagent (I) and tested with a fibrinogen assay apparatus CG01 (supplied by A & T Corp.) for the correlation between the fibrinogen concentration in an assay sample and tile coagulation time when the end point was set where the attenuation ratio to the peak value of motion signal of the magnetic particles was outside the viscosity variation range determined in the present invention.

The end points were set at points where the motion signal of the magnetic particles attenuated from its peak value by 3%, 30% and 60%, and the time from the addition of an assay sample to each end point was taken as a coagulation time. These points correspond to points where the viscosity increased to be 100/97 (about 1.03) times, 100/70 (about 1.43) times and 100/40 (about 2.5) times as large as the minimum value of the viscosity.

Figure 20:
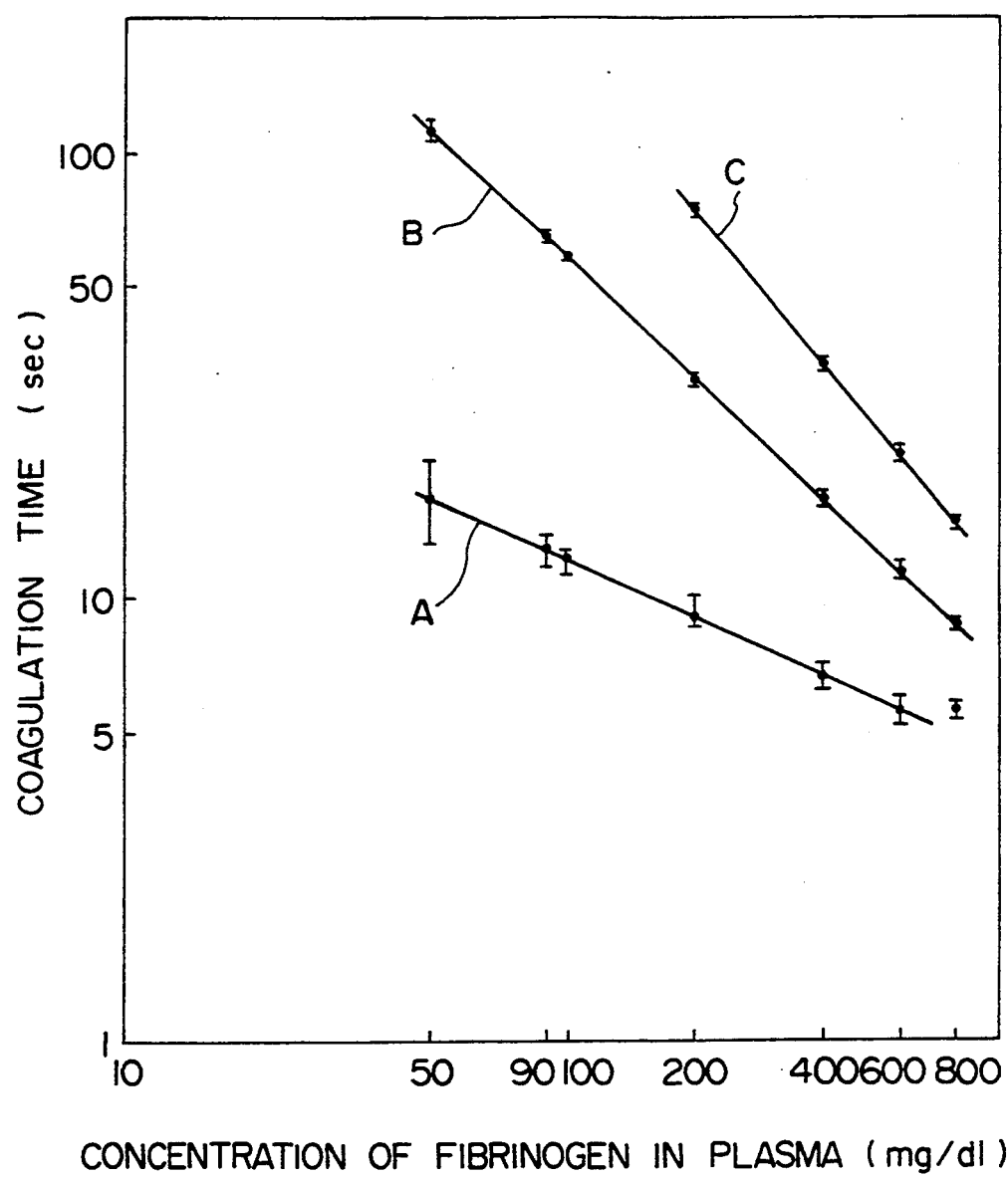
FIG. 20 shows the correlation between the coagulation time obtained when end points are set where the ratio of attenuation to the peak value of the motion signal of magnetic particles differs from that of the present invention and the fibrinogen concentration.

The correlation between the coagulation time and the fibrinogen concentration was examined as follows. A series of seven dilution solutions of human plasmas having fibrinogen concentrations of 50, 90, 100, 200, 400, 600 and 800 mg/dl were prepared from human plasma containing 800 mg/dl of fibrinogen and fibrinogen-deficient human plasma (supplied by George King Bio-Medical Inc.). Then, a series of these dilution solutions were$^I$ respectively diluted with an OWREN's buffer solution 20 times. The above freeze-dry reagent was set at a fibrinogen assaying apparatus CG01, and 25 µl of one of the above diluted solutions was added to determine the coagulation time of the diluted solution by the above method. In this manner, the coagulation times of all the diluted solutions were determined. The so-obtained data were plotted to draw an X-Y logarithmic graph in which the X-axis indicated fibrinogen concentration and the Y-axis indicated data of the coagulation time (average of three measurement data). The correlation was determined on the basis of the linearity of the drawn graph. FIG. 20 shows the correlation between the fibrinogen concentration and the coagulation time. In FIG. 20, A indicates a graph showing the relation between the coagulation time and the fibrinogen concentration when the motion signal of the magnetic particles attenuated from its peak value by 3%, B indicates a graph showing the same when the motion signal of the magnetic particles attenuated from its peak value by 30%, and C indicates a graph showing the same when the motion signal of the magnetic particles attenuated from its peak value by 60%. In each graph, each "." shows an average value obtained by measuring the coagulation time three times, and the length of each vertical line ("I") shows a deviation breadth of three measurement values.

FIG. 20 shows that when the end point is set where the motion signal of the magnetic particles attenuates from its peak value by 3%, there is a defect in that the fibrinogen assay cannot be performed accurately due to low sensitivity and poor reproducibility. Similarly, FIG. 20 shows that when the end point is set where the motion signal of the magnetic particles attenuates from its peak value by 60 the sensitivity is high, but there is a defect in that the assay range is narrow since no end point can be determined for plasma having a fibrinogen concentration of less than 200 mg/dl and the coagulation time therefore cannot be determined.

FIG. 20 clearly shows that when the end point is set where the motion signal of the magnetic particles attenuates from its peak value by 30%, the sensitivity is high, the assay range is broad and the reproducibility is excellent.

Example 12

Each of the following diluted plasmas (25 μl) having a fibrinogen concentration of 50 to 800 mg/dl was added to the same sodium glutamate reagent as that prepared in Example 1, and the mixture was measured with a measuring apparatus CG01 (supplied by A & T Corp.) for signals.

The diluted plasmas were prepared as follows. A high-concentration fibrinogen solution (FIBI, supplied by Enzyme Research Laboratories, Inc.) and normal plasma (supplied by George King Bio-Medical Inc.) were mixed to prepare plasma having a fibrinogen concentration of 1,100 mg/dl. The so-obtained plasma and a fibrinogen-deficient were mixed to prepare eight kinds of plasmas having fibrinogen concentrations of 800,600,400,300,200,150, 100 and 50 mg/dl. Each plasma was diluted with an OWREN's buffer solution (supplied by Sigma Chemical Company) 20 times to obtain diluted plasma solutions.

Signal waveforms obtained by the above measurement were converted to logarithmic signal waveforms, and periods of time (to be sometimes abbreviated as "pt" hereinafter) from the addition of the assay sample to a time when the reaction system showed a minimum viscosity were determined. The logarithmic waveforms were searched for linear regions which were considered to reflect the fibrinogen concentrations, and pt's were classified so that the assay ranges were included in the above regions. The assay ranges were determined as shown in Table 8. The viscosity increase rate in each assay range was calculated.

TABLE 3

| pt (second) | Assay range | | Time for assay range |
|---|---|---|---|
| | Start point | End point | |
| Less than 5 | pt + 2.5 | pt + 7.5 | 5.0 |
| 5 to 15 (exclusive) | pt + 7.5 | pt + 15.0 | 7.5 |
| 15 or more | pt + 17.5 | pt + 35.0 | 17.5 |

The viscosity increase rate in the assay range refers to a value obtained by dividing a change amount of logarithmic values of signal intensity from the start point of the assay range to the end point thereof by a period of time (seconds) from the start point to the end point, and it is a change ratio per unit time in the assay range.

Figure 21:
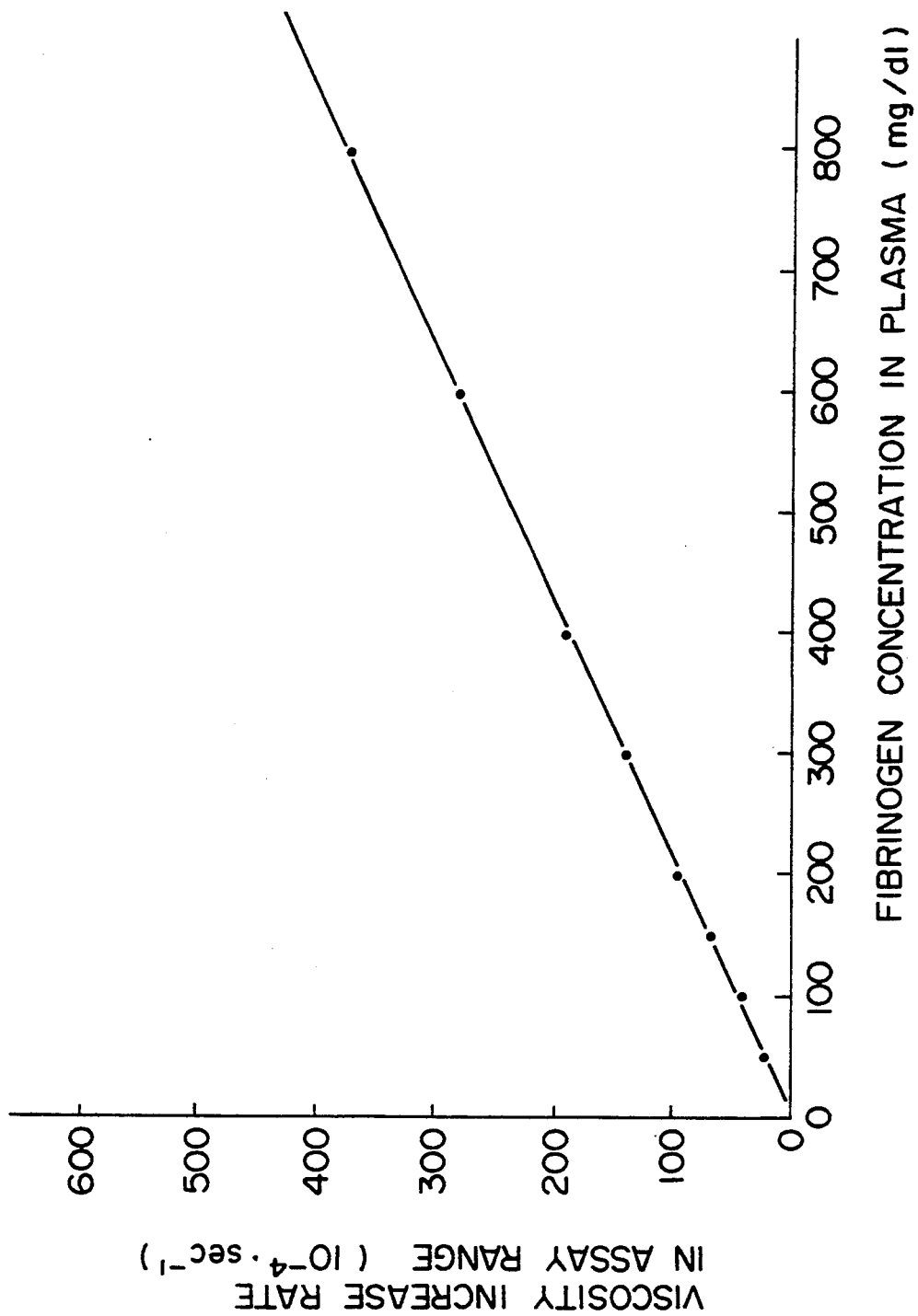
FIG. 21 shows the fibrinogen assay curve (calibration curve) obtained by determining the assay range corresponding to a time when the reaction system shows the minimum viscosity value, in which the abscissa axis indicates fibrinogen concentration and the ordinate axis indicates viscosity increase rate in the assay range.

Then, the relation between the viscosity increase rate and the fibrinogen concentration in the arrange range was examined. FIG. 21 shows the results, in which the abscissa axis indicates fibrinogen concentration and the ordinate axis indicates viscosity increase rate in the assay range. In FIG. 21, each dot shows an average of five measurements. FIG. 21 shows that eight kinds of the diluted plasmas had linear relationship between the viscosity increase rate in the assay range and the fibrinogen concentration. The correlation coefficient of this linearity was 0.99978, and excellent linearity was obtained. As described above, when the concentration ranged from 50 to 800 mg/dl, there was obtained a calibration curve showing the relationship between the viscosity increase rate in the assay range and the fibrinogen content.

Example 13

Twenty human plasma assay samples were diluted in the same manner as in Example 12 and added to the same sodium glutamate reagents as that prepared in Example 1. The resultant reaction systems were measured for Pt. And then the resultant reaction systems were measured for viscosity increase rates in the assay ranges corresponding to Pt in the same manner as in Example 12. The so-obtained viscosity increase rates of the above assay samples were converted to fibrinogen concentrations on the basis of the calibration curve prepared in Example 12.

The same assay samples as those used above were measured for fibrinogen values by a conventional assay method using a liquid reagent to examine the correlation to the fibrinogen values obtained above. The fibrinogen assay using a liquid reagent was carried out as follows. The reagent was Data-Fi.fibrinogen (supplied by International Reagents Corp.), and mixtures of the assay samples with this reagent were measured with a measuring apparatus KC-10A (supplied by Amelung GmbH, Lemgo) according to the instructions attached to Data-Fi.fibrinogen.

FIG. 22 shows the results, in which the abscissa axis indicates fibrinogen concentrations obtained by the conventional method, and the ordinate axis indicates fibrinogen concentrations obtained according to the present invention. On the basis of the results, the correlation coefficient was 0.98966 and the results obtained according to the present invention well correlated with those obtained by the conventional method.

What is claimed is:

1. A dry reagent for fibrinogen assay, consisting essentially of:
   (a) a protein having thrombin activity (component a),
   (b) at least one additive selected from the group consisting of acidic amino acids, basic amino acids, glycine, alanine, a salt of said amino acids, sucrose, lactose, trehalose, dextrin, glucose, and fructose (component b), and
   (c) magnetic particles (component c).

2. The dry reagent of claim 1, wherein, per 25 μl of a diluted assay sample for one measurement, said dry reagent consist essentially of:
   (a) 0.5 to 1.5 NIHU, as a thrombin amount, of the component a,
   (b) 0.02 to 1 mg of the component b, and
   (c) $2 \times 10^{-6}$ to $2 \times 10^{-4}$ g of the component c.

3. The dry reagent of claim 1, wherein the component a is a bovine thrombin, a human thrombin or a snake venom protein having thrombin activity.

4. The dry reagent of claim 1, wherein the component b is one of said amino acids or a salt thereof.

5. The dry reagent of claim 4, wherein the amino acid or tile salt thereof is α-amino acid or a salt thereof.

6. The dry reagent of claim 4, wherein the amino acid or tile salt thereof is an acidic amino acid or a salt thereof.

7. The dry reagent of claim 4, wherein the amino acid or the salt thereof is glutamic acid, sodium glutamate, aspattic acid or sodium aspartate.

8. The dry reagent of claim 1, wherein the component b is glucose, fructose or sucrose.

9. The dry reagent of claim 1, wherein the component c is ferrosoferric oxide particles.

10. A reaction slide for fibrinogen assay containing the dry reagent of claim 1 in a film form.

11. A process for the production of the dry reagent of claim 1 for fibrinogen assay, comprising freeze-drying a mixed liquid consisting essentially of:
    (a) a protein having thrombin activity (component a),
    (b) at least one additive selected from the group consisting of acidic amino acids, basic amino acids, glycine, alanine, a salt of said amino acids, sucrose, lactose, trehalose, dextrin, glucose, and fructose (component b),
    (c) magnetic particles (component c), and
    (d) water-based medium (component d).

12. The process of claim 11, wherein the component d is a buffer solution.

13. A dry reagent for fibrinogen assay, consisting essentially of:
    (a) a protein having thrombin activity (component a) and
    (b) at least one additive selected from the group consisting of acidic amino acids, basic amino acids, glycine, alanine, a salt of said amino acids, sucrose, lactose, trehalose, dextrin, glucose, and fructose (component b).

14. The dry reagent of claim 13, wherein, per 300 μl of a diluted assay sample for one measurement, said dry reagent consists essentially of:
    (a) 5 to 15 NIHU, as a thrombin amount, of the component a and
    (b) 0.2 to 10 mg of the component b.

15. The dry reagent of claim 13, wherein the component a is a bovine thrombin, a human thrombin or a snake venom protein having thrombin activity.

16. The dry reagent of claim 13, wherein the component b is one of said amino acids or a salt thereof.

17. The dry reagent of claim 16, wherein the amino acid or the salt thereof is α-amino acid or a salt thereof.

18. The dry reagent of claim 16, wherein the amino acid or the salt thereof is an acidic amino acid or a sale thereof.

19. The dry reagent of claim 16, wherein the amino acid or the salt thereof is glutamic acid, sodium glutamate, aspattic acid or sodium aspartate.

20. The dry reagent of claim 13, wherein the component b is glucose, fructose or sucrose.

21. A process for the production of the dry reagent of claim 13, comprising freeze-drying a mixed liquid consisting essentially of:
    (a) a protein having thrombin activity (component a),
    (b) at least one additive selected from the group consisting of acidic amino acids, basic amino acids, glycine, alanine, a salt of said amino acids, sucrose, lactose, trehalose, dextrin, glucose, and fructose (component b), and
    (d) water-based medium (component d).

22. The process of claim 21, wherein the component d is a buffer solution.

* * * * *